(12) United States Patent
Puttur et al.

(10) Patent No.: US 11,911,436 B2
(45) Date of Patent: Feb. 27, 2024

(54) AMPHIPHILIC PEPTIDE CHAPERONES AND METHODS OF USE

(71) Applicant: THE CURATORS OF THE UNIVERSITY OF MISSOURI, Columbia, MO (US)

(72) Inventors: Santhoshkumar Puttur, Columbia, MO (US); Krishna Sharma, Columbia, MO (US); Sundararajan Mahalingam, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 17/830,565

(22) Filed: Jun. 2, 2022

(65) Prior Publication Data

US 2022/0387548 A1 Dec. 8, 2022

Related U.S. Application Data

(60) Provisional application No. 63/195,876, filed on Jun. 2, 2021.

(51) Int. Cl.
| | |
|---|---|
| *A61K 38/10* | (2006.01) |
| *A61K 47/69* | (2017.01) |
| *A61K 47/54* | (2017.01) |
| *C12N 15/70* | (2006.01) |

(52) U.S. Cl.
CPC ............ *A61K 38/10* (2013.01); *A61K 47/542* (2017.08); *A61K 47/6929* (2017.08); *C12N 15/70* (2013.01)

(58) Field of Classification Search
None
See application file for complete search history.

(56) References Cited

FOREIGN PATENT DOCUMENTS

WO 2013/184209 A1 12/2013

OTHER PUBLICATIONS

Baranyi, L. et al. (1995). The antisense homology box: a new motif within proteins that encodes biologically active peptides. Nature medicine, 1(9), 894-901.
Raju, M. et al. (2018). Cell-Penetrating Chaperone Peptide Prevents Protein Aggregation and Protects against Cell Apoptosis. Advanced Biosystems, 2(1), 1700095, 21 pages.
Santhoshkumar, P. et al. (2020). A cell-penetrable mini-chaperone extends the lifespan of Caenorhabditis elegans and alleviates β amyloid-induced toxicity. Investigative Ophthalmology & Visual Science, 61(7), 2 pages. (Conference Abstract).
Sharma, K. K. et al. (2019). Minichaperones inhibit the hemolytic activity of Mellitin. Investigative Ophthalmology & Visual Science, 60(9), 2 pages.
Sreekumar, P. G. et al. (2013). Antiapoptotic properties of α-crystallin-derived peptide chaperones and characterization of their uptake transporters in human RPE cells. Investigative ophthalmology & visual science, 54(4), 2787-2798.

*Primary Examiner* — Sergio Coffa
(74) *Attorney, Agent, or Firm* — Stinson LLP

(57) ABSTRACT

The present disclosure provides amphiphilic peptide chaperones. Also provided are their incorporation into pharmaceutical compositions and methods of use for preventing or reducing a source of stress in cells and for the treatment of disorders including Alzheimer's disease, Parkinson's disease, amyotrophic lateral sclerosis (ALS), cataract, age-related macular degeneration (AMD), glaucoma, and retinitis pigmentosa.

6 Claims, 31 Drawing Sheets
Specification includes a Sequence Listing.

Figure 1

Sequence interpretation

Single letter code: Ac- LFVIFLVHFS PGRDEDKDEK -CONH2 (SEQ ID NO: 8)
Triple letter code: Ac- Leu - Phe - Val - Ile - Phe - Leu - Val - His - Phe - Ser - Pro - Gly - Arg - Asp - Glu - Asp - Lys - Asp - Glu - Lys -CONH2 (SEQ ID NO: 8)

Physiochemical properties

Number of residues: 20
Molecular weight: 2432.73 g/mol   notes on MW
Extinction coefficient: 0 M$^{-1}$cm$^{-1}$   notes on Ext. Coefficient
Iso-electric point: pH 4.5   notes on pI
Net charge at pH 7: -1.9   notes on net charge
Estimated solubility: Good water solubility.   notes on solubility

Net charge vs pH

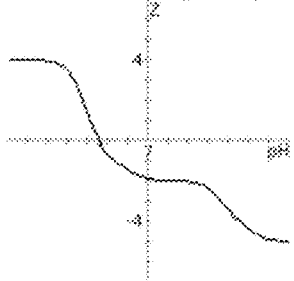

Hydropathy   Hopp & Woods

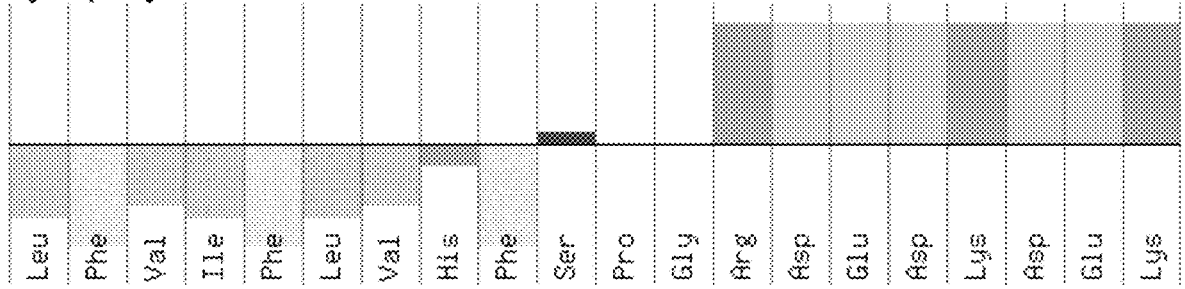

Top is hydrophilic
Bottom is hydrophobic
Color codes:   Acidic   Aromatic   Basic   Aliphatic   Polar   Cysteine 2 μM Melittin
+
Myr-CPAMC

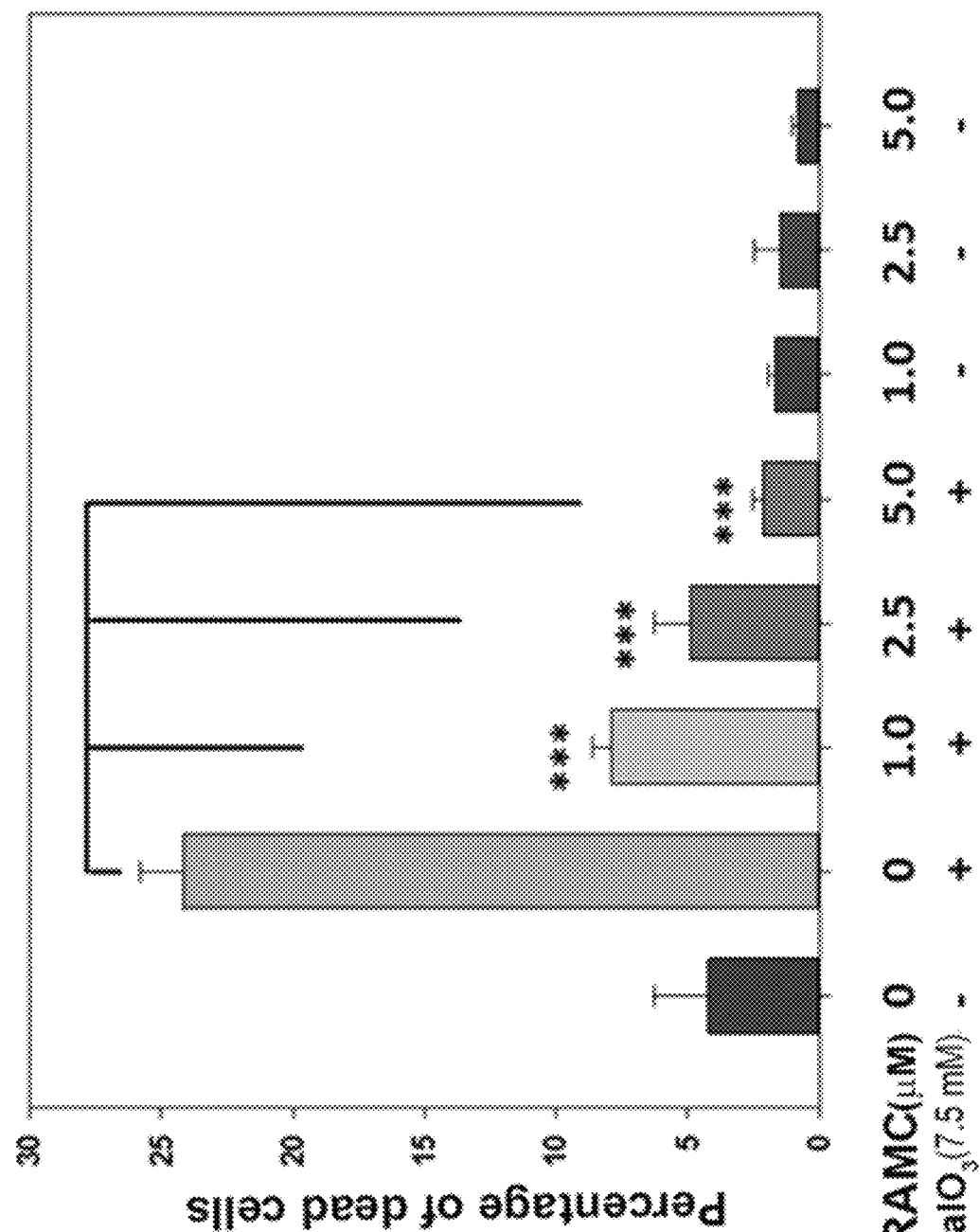

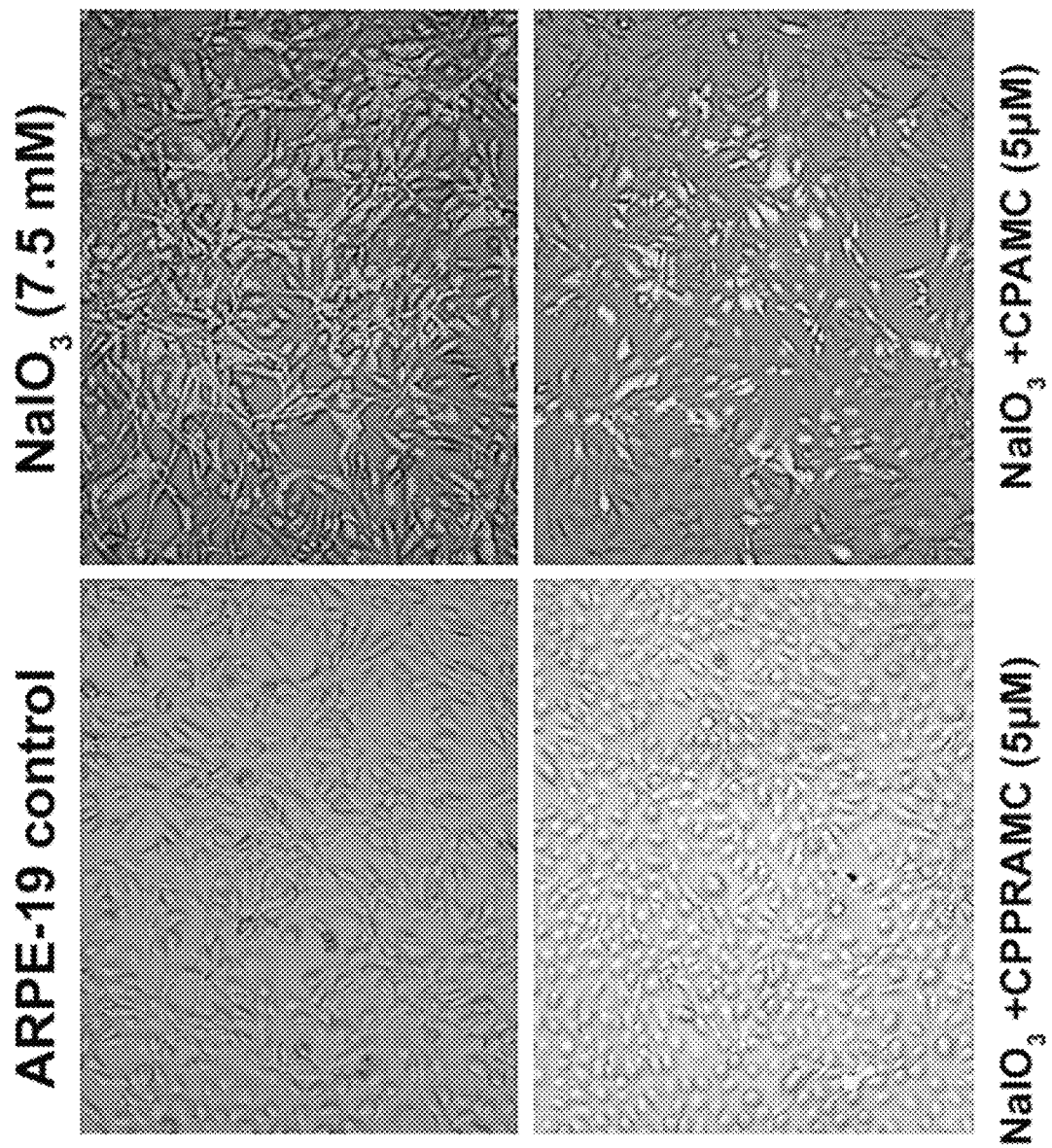

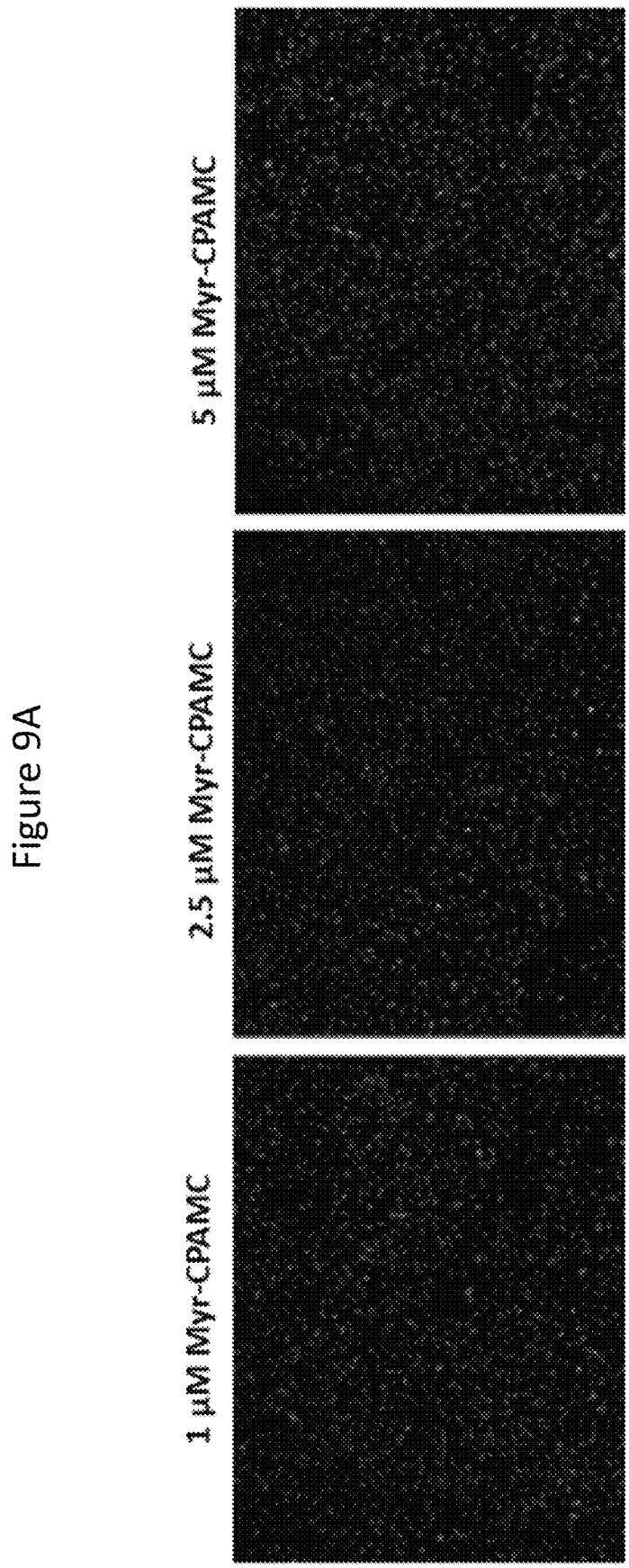

Kaplan-Meier Survival Analysis

Schematic representation of CL4176 paralysis assay

SEQUENCE LISTING

<160> NUMBER OF SEQ ID NOS: 8

<210> SEQ ID NO 1
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: METHYLATION
<222> LOCATION: (1)..(1)
<220> FEATURE:
<221> NAME/KEY: AMIDATION
<222> LOCATION: (20)..(20)

<400> SEQUENCE: 1

Leu Phe Val Ile Phe Leu Val His Phe Ser Pro Gly Arg Asp Glu Asp
1               5                   10                  15

Lys Asp Glu Lys
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MYRISTATE
<222> LOCATION: (1)..(1)
<220> FEATURE:
<221> NAME/KEY: AMIDATION
<222> LOCATION: (21)..(21)

<400> SEQUENCE: 2

Lys Leu Phe Val Ile Phe Leu Val His Phe Ser Pro Gly Arg Asp Glu
1               5                   10                  15

Asp Lys Asp Glu Lys
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MYRISTATE
<222> LOCATION: (1)..(1)
<220> FEATURE:
<221> NAME/KEY: MOD_RES
<222> LOCATION: (1)..(2)
<223> OTHER INFORMATION: Tetramethylrhodamine (TMR)-labeled
<220> FEATURE:
<221> NAME/KEY: AMIDATION
<222> LOCATION: (21)..(21)

<400> SEQUENCE: 3

Lys Leu Phe Val Ile Phe Leu Val His Phe Ser Pro Gly Arg Asp Glu
1               5                   10                  15

Asp Lys Asp Glu Lys
            20

<210> SEQ ID NO 4
<211> LENGTH: 28
<212> TYPE: PRT
<213> ORGANISM: Artificial Sequence
<220> FEATURE:
<223> OTHER INFORMATION: Synthetic

```
<220> FEATURE:
<221> NAME/KEY: METHYLATION
<222> LOCATION: (1)..(1)
<220> FEATURE:
<221> NAME/KEY: DOMAIN
<222> LOCATION: (21)..(28)
<223> OTHER INFORMATION: FLAG tag
<220> FEATURE:
<221> NAME/KEY: AMIDATION
<222> LOCATION: (28)..(28)

<400> SEQUENCE: 4

Leu Phe Val Ile Phe Leu Val His Phe Ser Pro Gly Arg Asp Glu Asp
1               5                   10                  15

Lys Asp Glu Lys Asp Tyr Lys Asp Asp Asp Lys
            20                  25

<210> SEQ ID NO 5
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: METHYLATION
<222> LOCATION: (1)..(1)
<220> FEATURE:
<221> NAME/KEY: AMIDATION
<222> LOCATION: (19)..(19)

<400> SEQUENCE: 5

Asp Phe Val Ile Phe Leu Asp Val Lys His Phe Ser Pro Glu Asp Leu
1               5                   10                  15

Thr Val Lys

<210> SEQ ID NO 6
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: METHYLATION
<222> LOCATION: (1)..(1)
<220> FEATURE:
<221> NAME/KEY: PHOSPHORYLATION
<222> LOCATION: (10)..(10)
<220> FEATURE:
<221> NAME/KEY: AMIDATION
<222> LOCATION: (20)..(20)

<400> SEQUENCE: 6

Leu Phe Val Ile Phe Leu Val His Phe Ser Pro Gly Arg Asp Glu Asp
1               5                   10                  15

Lys Asp Glu Lys
            20

<210> SEQ ID NO 7
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<220> FEATURE:
<221> NAME/KEY: DOMAIN
<222> LOCATION: (21)..(28)
<223> OTHER INFORMATION: FLAG tag
```

```
<220> FEATURE:
<221> NAME/KEY: AMIDATION
<222> LOCATION: (28)..(28)

<400> SEQUENCE: 7

Leu Phe Val Ile Phe Leu Val His Phe Ser Pro Gly Arg Asp Glu Asp
1               5                   10                  15

Lys Asp Glu Lys Asp Tyr Lys Asp Asp Asp Lys
            20              25

<210> SEQ ID NO 8
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<220> FEATURE:
<221> NAME/KEY: AMIDATION
<222> LOCATION: (20)..(20)

<400> SEQUENCE: 8

Leu Phe Val Ile Phe Leu Val His Phe Ser Pro Gly Arg Asp Glu Asp
1               5                   10                  15

Lys Asp Glu Lys
            20
```

AMPHIPHILIC PEPTIDE CHAPERONES AND METHODS OF USE

REFERENCE TO RELATED APPLICATIONS

This application claims the benefit of U.S. Provisional Patent Application No. 63/195,876, filed Jun. 2, 2021, the entire disclosure of which is incorporated herein by reference.

STATEMENT REGARDING FEDERALLY SPONSORED RESEARCH OR DEVELOPMENT

This invention was made with government support under Contract Nos. R21EY029393 and R01EY023219 awarded by the National Institutes of Health (NIH) (NEI). The government has certain rights in the invention.

INCORPORATION OF SEQUENCE LISTING

A paper copy of the Sequence Listing and a computer readable form of the Sequence Listing containing the file named "21UMC068 Sequence Listing Replacement 03.29.2023_ST25," which is 3,651 bytes in size (as measured in MICROSOFT WINDOWS® EXPLORER) and was created on Mar. 29, 2023, are provided herein and are herein incorporated by reference. This Sequence Listing consists of SEQ ID NOs: 1-8.

FIELD OF INVENTION

The present disclosure relates to amphiphilic peptide chaperones, pharmaceutical compositions comprising these amphiphilic peptide chaperones, and their methods of use. More specifically, the present disclosure relates to their use in preventing or reducing a source of stress in cells or a patient and/or the treatment of a disorder such as paralysis, COVID-19, COVID-19 mutant, diabetes, Alzheimer's disease, Parkinson's disease, amyotrophic lateral sclerosis (ALS), cataract, age-related macular degeneration (AMD), glaucoma, or retinitis pigmentosa.

BACKGROUND OF INVENTION

Diverse protein conformational diseases, including Alzheimer's, Parkinson's disease, amyotrophic lateral sclerosis, cataract, retinitis pigmentosa, etc., follow a common structural and pathological pathway. Therapeutic interventions to prevent, delay, or stop the accumulation of misfolded proteins and associated diseases would significantly reduce health care costs and the burden of suffering from such conditions. Medical expenses for the many protein conformational diseases drive up health care costs by tens of billions of dollars. The development of therapies for such diseases is intrinsic to reducing costs and improving the quality of life in the elderly. Under development as frontline therapies to prevent protein misfolding and the ensuing cellular dysfunction and death are various molecular chaperones, including small molecules and protein and peptide chaperones that selectively bind to and stabilize the target proteins. However, the majority of chaperones tested thus far lack in vivo specificity or act against only one of the several pathological events associated with the disease.

SUMMARY OF INVENTION

The disclosure provides amphiphilic peptide chaperones and their incorporation into pharmaceutical compositions and their methods of use.

In one aspect, the disclosure is directed to an amphiphilic peptide chaperone comprising an amino acid sequence having at least 80% identity to LFVIFLVHFSPGRDEDKDEK (SEQ ID NO: 1) or lfviflvhfspgrdedkdek.

Another aspect of the disclosure is a nucleic acid comprising a nucleotide sequence encoding the peptide of the amphiphilic peptide chaperone, an expression vector comprising the nucleic acid, and a host cell comprising the expression vector.

Yet another aspect of the invention is a pharmaceutical composition, wherein the composition comprises the above amphiphilic peptide chaperone.

A further aspect of the disclosure is a method of preventing or treating a disorder in a subject in need thereof, the method comprising administering to the subject a therapeutically effective amount of the pharmaceutical composition.

BRIEF DESCRIPTION OF DRAWINGS

FIG. 1 depicts CPAMC properties, including sequence interpretation, physiochemical properties, net charge vs. pH, and hydropathy of individual amino acids.

FIG. 6B depicts a quantification of the cell viability imaging data exemplified in FIG. 6A. The data shown is an average of six analyses performed on images captured from different wells. *** indicates p-value<0.005.

FIG. 6C depicts the suppression of sodium iodate-induced oxidative stress in ARPE-19 cells by CPPRAMC and CPAMC peptides.

FIG. 9A depicts cell viability imaging performed in the presence of increasing concentrations of Myr-CPAMC, with dead cells identified by fluorescent staining.

DETAILED DESCRIPTION OF INVENTION

Figure 2A:
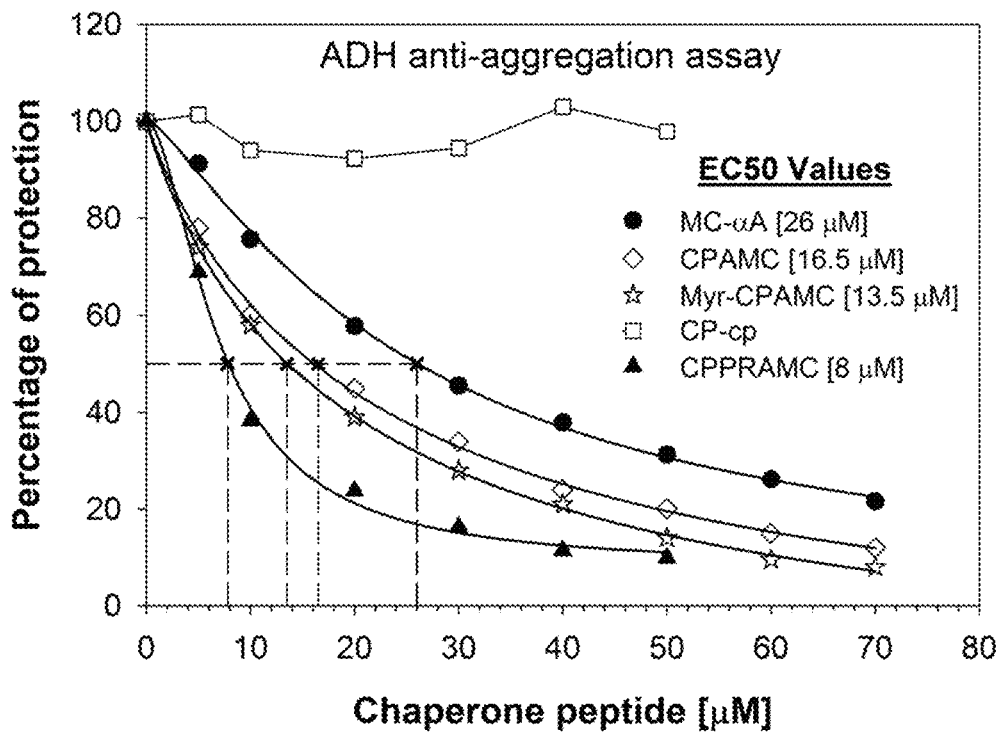
FIG. 2A depicts an ADH anti-aggregation assay for MC-αA, CPAMC, Myr-CPAMC, CP-cp, and CPPRAMC peptides.

This description is merely exemplary in nature and is in no way intended to limit the present teachings, application, or uses. Throughout this specification, like reference numerals are used to refer to like elements.

Amphiphilic Peptide Chaperone

The present disclosure is directed to an amphiphilic peptide chaperone comprising an amino acid sequence having at least 80% identity to LFVIFLVHFSPGRDEDKDEK (SEQ ID NO: 1) or lfviflvhfspgrdedkdek. The amino acid sequence can have at least 90%, at least 95%, at least 99%, or at least 99.9% sequence identity to LFVIFLVHFSPGRDEDKDEK (SEQ ID NO: 1) or lfviflvhfspgrdedkdek. The amino acid sequence can comprise or consist of LFVIFLVHFSPGRDEDKDEK (SEQ ID NO: 1) or lfviflvhfspgrdedkdek. The chaperone can comprise an analog or derivative of a peptide comprising an amino acid sequence LFVIFLVHFSPGRDEDKDEK (SEQ ID NO: 1) or lfviflvhfspgrdedkdek. The amino acid sequence can comprise a variant of LFVIFLVHFSPGRDEDKDEK (SEQ ID NO: 1) or lfviflvhfspgrdedkdek with at least one insertion, deletion, or substitution.

The amino acid sequence can include only L-amino acids or the amino acid sequence includes only D-amino acids. The amino acid sequence can include only D-amino acids, and the peptide chaperone comprising the amino acid sequence including only D-amino acids can have increased stability and biological activity compared to the peptide chaperone comprising the amino acid sequence including only L-amino acids. Uppercase letters indicate L-amino acids, and lowercase letters indicate D-amino acids.

The chaperone can further comprise at least one chemical modification selected from the group consisting of myristoylation, phosphorylation, acetylation, methylation, glycosylation, ADP-ribosylation, amidation, lipid addition, oxidation, palmitoylation, FLAG tagging, and tetramethylrhodamine labeling. The chaperone can be conjugated with one or more fatty acids to improve peptide pharmacokinetics. The chaperone can be myristoylated and/or labeled with tetramethylrhodamine. The N-terminus of the amino acid sequence can be myristoylated and/or labeled with tetramethylrhodamine; preferably, the N-terminus of the amino acid sequence is labeled with tetramethylrhodamine and then myristoylated. The C-terminus of the amino acid sequence can be FLAG tagged. At least one amino acid of the amino acid sequence can be phosphorylated; preferably, the amino acid sequence comprises LFVIFLVHF{pSer}PGRDEDKDEK (SEQ ID NO: 6), wherein {pSer} indicates a phosphorylated serine amino acid. For any of the chaperones of this disclosure, the N-terminus of the amino acid sequence can have a $CH_3$ modification and/or the C-terminus of the amino acid sequence can have a $NH_2$ modification.

Preferably, the chaperone can have cell-penetrating and protease-resistant properties and is non-toxic to cells. The chaperone can also help maintain cellular homeostasis and increase longevity. The chaperone can protect cells and tissues from oxidative stress and apoptosis. Preferably, the chaperone assists in protein folding or refolding during or after synthesis.

The chaperone can have the ability to self-assemble with other like chaperones as spherical nanoparticles. Preferably, the nanoparticles are about 20-30 nm in diameter.

The chaperone can prevent or reduce a source of stress in cells. Preferably, the source of stress is selected from the list consisting of beta-amyloid oligomerization and deposition, induced cytotoxicity, oxidative stress, protein aggregation, inflammation, apoptosis, hyperglycemia, hemolytic activity of melittin, aging, and heat stress. Most preferably, the source of stress leads to aggregated protein.

The chaperone or peptide can be expressed using a transgenic cell line or a transgenic organism. A nucleic acid can be made comprising a nucleotide sequence encoding the peptide of any of the chaperones described in this disclosure. This nucleic acid can then be incorporated into an expression vector. The expression vector can further comprise other components, such as tags for the chaperone and promoters to promote expression of the chaperone in one or more organisms. Exemplary tags include GFP and FLAG tags. A host cell and/or organism comprising the expression vector can express the chaperone.

As used herein, "amphiphilic" indicates a compound or peptide has both hydrophilic and hydrophobic moieties.

As used herein, a "chaperone" is a protein or peptide that helps in the correct folding of peptides or proteins, prevents peptide or protein aggregation, blocks the formation of toxic aggregates, and helps in the secretion of peptides or proteins from cells.

As used herein, a "transgenic" cell line or organism refers to a cell line or organism that has had an exogenous nucleic acid sequence introduced to its genome. Introduction of the exogenous nucleic acid sequence can be performed with any transformation method commonly known in the art, which can include but is not limited to CRISPR-Cas9-mediated transformation and viral infection. The cell line can be an immortalized or primary cell line.

Pharmaceutical Composition

A pharmaceutical composition can be formulated, wherein the composition comprises one or more of the amphiphilic peptide chaperones described above. The composition can have similar properties to the amphiphilic peptide chaperones described above. The composition can help maintain cellular homeostasis in a subject. The composition can also prevent or reduce a source of stress in cells of a subject. Preferably, the source of stress is selected from the list consisting of beta-amyloid oligomerization and deposition, induced cytotoxicity, oxidative stress, protein aggregation, inflammation, apoptosis, hyperglycemia, the hemolytic activity of melittin, aging, and heat stress.

The composition can be useful for preventing or treating a disorder in a subject in need thereof. Preferably, the disorder is selected from the group consisting of paralysis, COVID-19, COVID-19 mutant, diabetes, Alzheimer's disease, Parkinson's disease, amyotrophic lateral sclerosis (ALS), cataract, retinitis pigmentosa, age-related macular degeneration (AMD), and glaucoma. The disorder can also be a protein conformational disease. Preferably, the protein conformational disease is selected from the list consisting of Alzheimer's disease, Parkinson's disease, amyotrophic lateral sclerosis (ALS), cataract, age-related macular degeneration (AMD), glaucoma, and retinitis pigmentosa. The disorder can also be the result of bee venom toxin.

The pharmaceutical composition can also be formulated such that the chaperone comprises from about 0.001 to about 99.9%, about 0.001 to about 0.01%, about 0.01 to about 0.1%, about 0.1 to about 1%, about 1 to about 10%, about 10 to about 20%, about 20 to about 30%, about 30 to about 40%, about 50 to about 60%, about 60 to about 70%, about 80 to about 90%, or about 90 to about 99.9% of the total weight of the composition. The composition can further comprise a pharmaceutically acceptable excipient, carrier, and/or drug delivery agent. The composition can also further comprise an additional therapeutic small molecule.

Preferably, the composition can be administered parentally, intramuscularly, intravenously, intradermally, intranasally, or via targeted delivery. Preferably, the targeted delivery comprises injection.

The chaperone can also be self-assembled with other like chaperones as spherical nanoparticles. Preferably, these nanoparticles are about 20-30 nm in diameter. The nanoparticles can also be loaded with an additional therapeutic small molecule for targeted delivery. Preferably, the additional therapeutic small molecule is an anti-oxidant. When the chaperones are self-assembled with other like chaperones as spherical nanoparticles, the dosage can vary with the type of disease condition. For Alzheimer's disease, where there is a slow and progressive accumulation of misfolded proteins, multiple dosages may be required.

The peptides can also be delivered via extracellular vesicles. The extracellular vesicles can also be loaded with an additional therapeutic small molecule. Preferably, the additional therapeutic small molecule is an anti-oxidant. Preferably, a lower dosage of peptides is required when delivered via extracellular vesicles compared to the dosage of peptides required when not delivered via extracellular vesicles.

Methods of Use

Another aspect of the disclosure is a method of preventing or treating a disorder in a subject in need thereof, the method comprising administering to the subject a therapeutically effective amount of any of the pharmaceutical compositions described elsewhere in this disclosure.

Preferably, the disorder causes a symptom selected from the list consisting of beta-amyloid oligomerization and deposition, induced cytotoxicity, oxidative stress, protein aggregation, inflammation, apoptosis, hyperglycemia, the hemolytic activity of melittin, and heat stress.

Preferably, the disorder is selected from the group consisting of paralysis, COVID-19, COVID-19 mutant, diabetes, Alzheimer's disease, Parkinson's disease, amyotrophic lateral sclerosis (ALS), cataract, glaucoma, age-related macular degeneration (AMD), and retinitis pigmentosa.

Preferably, the disorder is a protein conformational disease. More preferably, the protein conformational disease is selected from the list consisting of Alzheimer's disease, Parkinson's disease, amyotrophic lateral sclerosis (ALS), cataract, age-related macular degeneration (AMID), glaucoma, and retinitis pigmentosa.

The disorder can also be the result of bee venom toxin, and melittin can be present in the subject.

The subject can be a nematode or a mammal. The subject is preferably a human.

The method preferably results in transcriptional changes in the subject. Preferably, the method alters the transport and catabolism pathways (cellular processes), energy metabolism pathways, and amino acid metabolism pathways.

EXAMPLES

The following non-limiting examples are provided to further illustrate the present invention and further provides several examples of the amphiphilic peptide chaperones and their use.

Example 1: Peptides and Chaperone Activities

The current disclosure is directed to using cell-penetrable amphiphilic peptide chaperones (CPAMCs), also called second-generation mini-chaperone peptides, to suppress protein aggregation and maintain cellular homeostasis in disease states. The CPAMC can be synthesized with D amino acids having protease-resistant properties (CPPRAMC). The CPAMC exhibits anti-aggregation activity in vitro against denaturing protein substrates. The CPPRAMC showed increased stability and biological activity. CPAMCs can be conjugated with fatty acids to improve peptide pharmacokinetics. The peptides self-assemble as spherical nanoparticles and can be loaded with small therapeutic molecules for targeted delivery.

TABLE 1

List of Peptides and their attributes

| Peptide name (SEQ ID NO) | Sequence | Attributes |
| --- | --- | --- |
| CPAMC (SEQ ID NO: 1) | $CH_3$-LFVIFLVHFSPGRDEDKDEK-$NH_2$ | Cell-penetrable, amphiphilic mini chaperone synthesized with L-amino acids tested in cell culture systems and *C. elegans*. |
| CPPRAMC | $CH_3$-lfviflvhfspgrdedkdek-$NH_2$ | Cell-penetrable, protease-resistant amphiphilic mini chaperone. Lead test compound synthesized using D-amino acids. It exhibits anti-aggregation, anti-oxidative, anti-inflammatory, and anti-apoptotic properties. |
| Myr-CPAMC (SEQ ID NO: 2) | Myristoyl-KLFVIFLVHFSPGRDEDKDEK-$NH_2$ | Lipid-conjugated amphiphilic peptide |
| Myr-(TAM)-CPAMC/ (SEQ ID NO: 3) | Myristoyl-{K(TMR)}LFVIFLVHFSPGRDEDKDEK-$NH_2$ | Lipid-conjugated, TMR-labeled peptide |
| CPAMC-FLAG (SEQ ID NO: 4) | $CH_3$-LFVIFLVHFSPGRDEDKDEKDYKDDDDK-$NH_2$ | CPAMC conjugated to FLAG peptide to be used for identifying target proteins and validating mini-gene expression products. |
| d-sc | $CH_3$-grfdlhfdelfkipvdsevk-$NH_2$ | Scrambled peptide synthesized using D-amino acids. Inactive peptide to be used as a control. |

TABLE 1-continued

List of Peptides and their attributes

| Peptide name (SEQ ID NO) | Sequence | Attributes |
|---|---|---|
| CP-cp (also referred to as CP-sc) | CH₃-VPTLKdlplknvedkfhrsfvesvk-NH₂ | Cell-penetrable, control peptide. Inactive peptide to be used as a control. |
| MC-αA (SEQ ID NO: 5) | CH₃-DFVIFLDVKHFSPEDLTVK-NH₂ | Parent peptide from αA crystallin for use in cell culture studies and in C. elegans. |
| p-CPAMC (SEQ ID NO: 6) | CH₃-LFVIFLVHF{pSer}PGRDEDKDEK-NH₂ | Phosphorylated peptide |
| Ac-FLAG (SEQ ID NO: 7) | Ac-LFVIFLVHFSPGRDEDKDEK DYKDDDDK-NH₂ | Acetylated and FLAG-tagged peptide |

In Table 1 and elsewhere in this disclosure, lowercase letters indicate peptides made using D amino acids. Uppercase letters indicate peptides made using L amino acids. Peptides are indicated as being synthesized with N-terminal $CH_3$ and C-terminal $NH_2$ modifications. Other potential peptides include but are not limited to any of the above peptides synthesized with N- or C-terminal FITC or TAMRA/TMR label to monitor peptide entry and fate.

Phosphorylated peptides (LFVIFLVHF{pSer}PGRDEDKDEK) (SEQ ID NO: 6) and peptides having an extended C-terminal arrangement with a FLAG tag ($CH_3$-LFVIFLVHFSPGRDEDKDEKDYKDDDDK-$NH_2$) (SEQ ID NO: 4) may be incorporated into the CPAMC. It has been observed that adding a FLAG tag to the C-terminal end does not alter the anti-aggregation activity of the peptide.

Figure 2B:
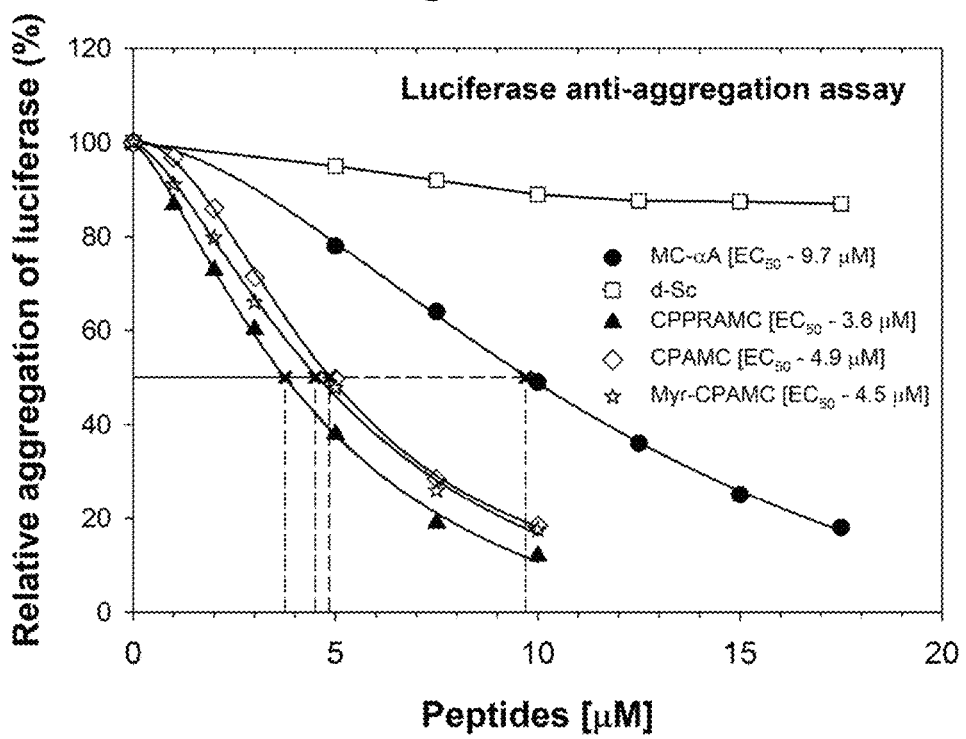
FIG. 2B depicts a luciferase anti-aggregation assay for MC-αA, d-Sc, CPPRAMC, CPAMC, and Myr-CPAMC peptides.

Properties of CPAMC are shown (FIG. 1). The peptide has amphiphilic structure. It possesses both hydrophobic and hydrophilic moieties and tends to self-assemble Relative chaperone activities of CPAMC, CPPRAIVIC, and Myr-CPAMC peptides were tested (FIG. 2A-2B). For FIG. 2A, the aggregation of alcohol dehydrogenase (ADH) (75 µg) was performed in 0.25 ml of PBS containing 50 mM EDTA in the presence of (0-70 µM) peptides. The kinetic assays were monitored at 360 nm in a Spectramax (Molecular devices) plate reader at 37° C. The amount of chaperone protein required to prevent the aggregation of the substrate by 50% (EC50) was calculated from the non-linear regression analysis. For FIG. 2B, the aggregation of luciferase (0.5 µM) was performed in 0.25 ml of PBS containing in the presence of (0-17.5 µM) peptides. The kinetic assays were monitored at 360 nm in a Spectramax (Molecular devices) plate reader at 37° C. The amount of chaperone protein required to prevent the aggregation of the substrate by 50% (EC50) was calculated from the non-linear regression analysis. The CPAMC peptides suppressed ADH (75 µg) and luciferase (0.5 µM) aggregation at 37° C., demonstrating chaperone activity.

Example 2: Suppression of Hemolytic Activity of Melittin with Peptide

Various amphiphilic peptide chaperones were shown to suppress hemolytic activity of melittin, a major component of bee venom.

Figure 3:
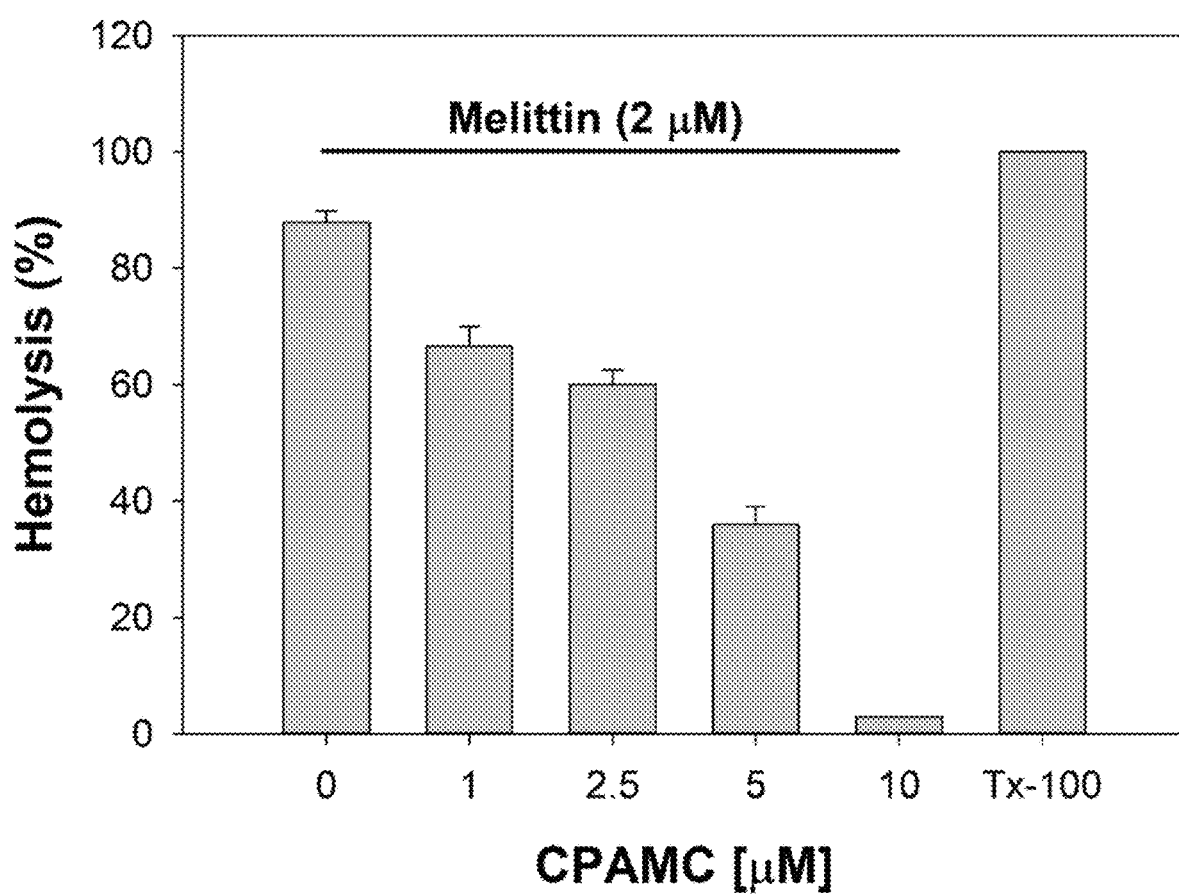
FIG. 3 depicts hemolytic activity of melittin in the presence of Triton-X 100 (Tx-100) or increasing concentrations of CPAMC peptide.

Hemolysis of human red blood cells with melittin was measured with varying concentrations of CPAMC (FIG. 3). To 0.3 mL of 2% human RBC (red blood cell) suspension was added 2 µM melittin and/or peptides taken in 0.7 mL of PBS. The tubes were incubated at room temperature for 30 min, centrifuged, and the OD of the supernatant was measured at 540 nm. PBS and PBS containing 0.1% TritonX-100 served as negative and positive control, respectively. Hemolysis decreased as concentration of CPAMC increased.

Figure 4A:
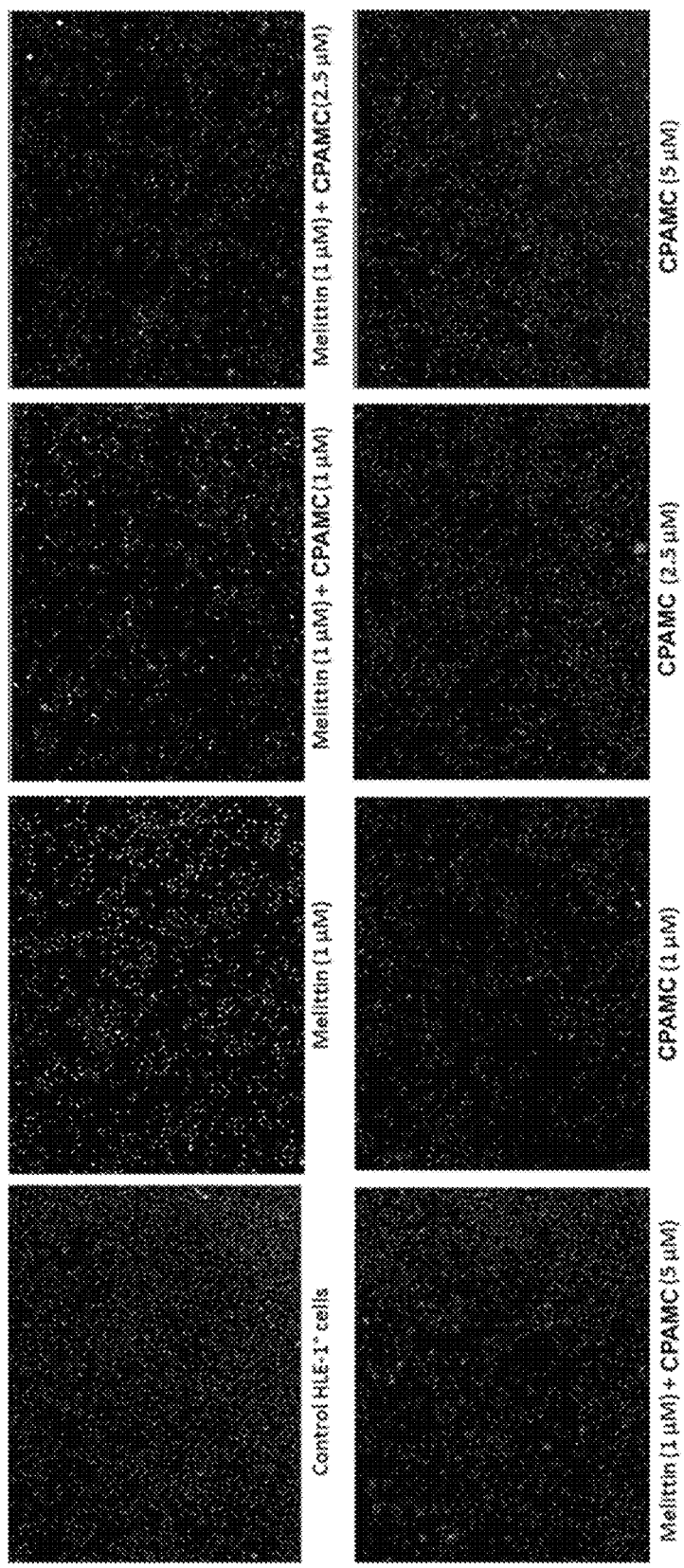
FIG. 4A depicts cell viability imaging of human primary lens epithelial (HLE-1°) cells in the presence of melittin and/or CPAMC peptide.
Figure 4B:
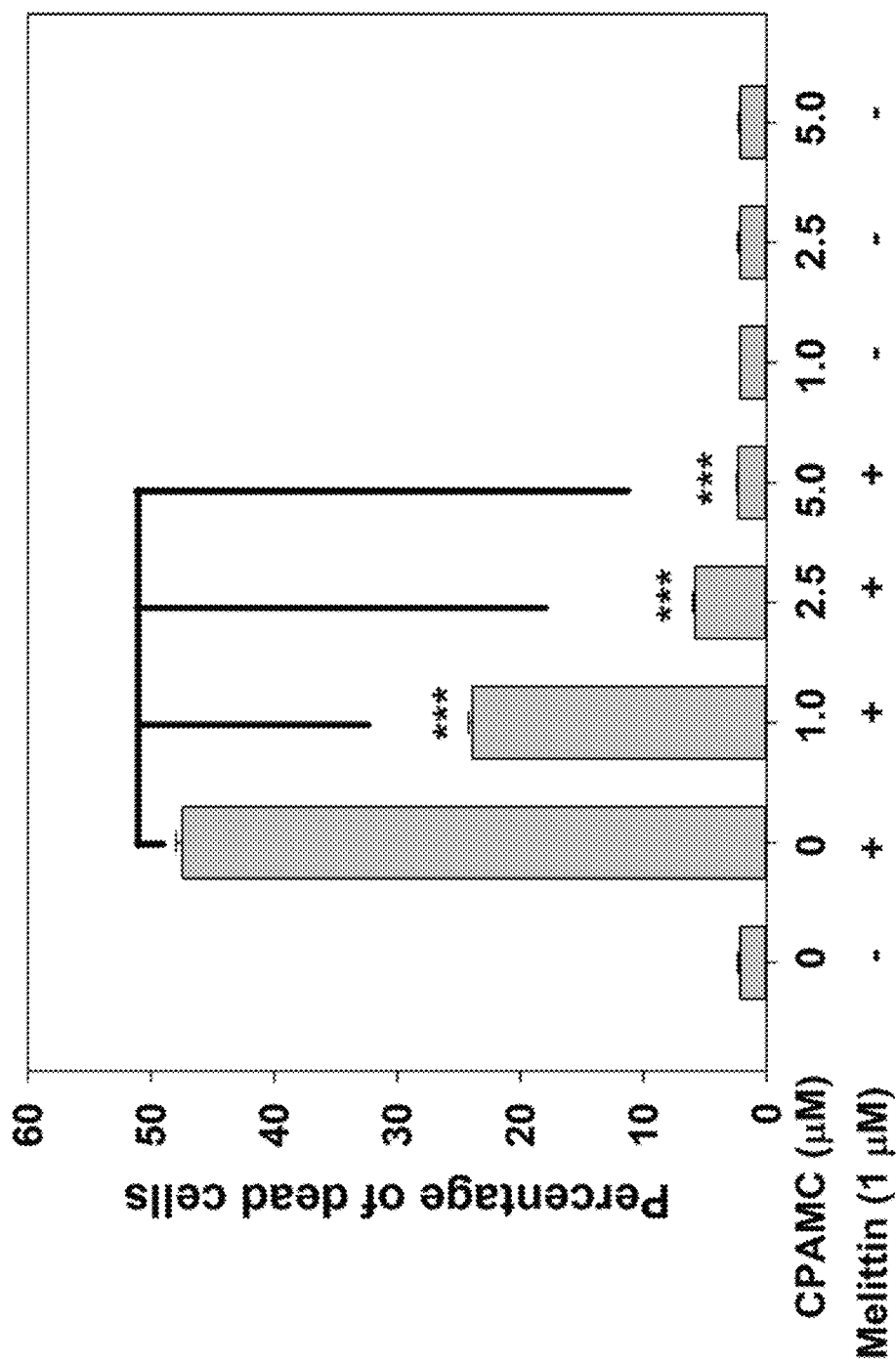
FIG. 4B depicts a quantification of the cell viability imaging data exemplified in FIG. 4A. The data shown is an average of six analyses performed on images captured from different wells. *** indicates p-value<0.005.

The ability of CPAMC peptide to block the cytotoxic action of melittin on human primary lens epithelial (HLE-1°) cells was investigated. Cell viability imaging was performed with dead cells identified by fluorescent staining. HLE-1° cells cultured on a 96-well plate were treated with 1 µM melittin and/or different concentrations of CPAMC peptide for 45 min. At the end of the incubation, cell viability imaging was done using the EarlyTox cell integrity kit (Molecular Devices, Sunnyvale, Calif.) (FIG. 4A). The percentage of dead cells in each sample was calculated from the live/dead cell imaging data using the Softmax Pro software (FIG. 4B). The percentage of dead cells in the presence of melittin decreased as CPAMC concentration increased (FIG. 4B), indicating that CPAMC also blocks the cytotoxic action of melittin on human primary lens epithelial (HLE-1°) cells.

Figure 5A:
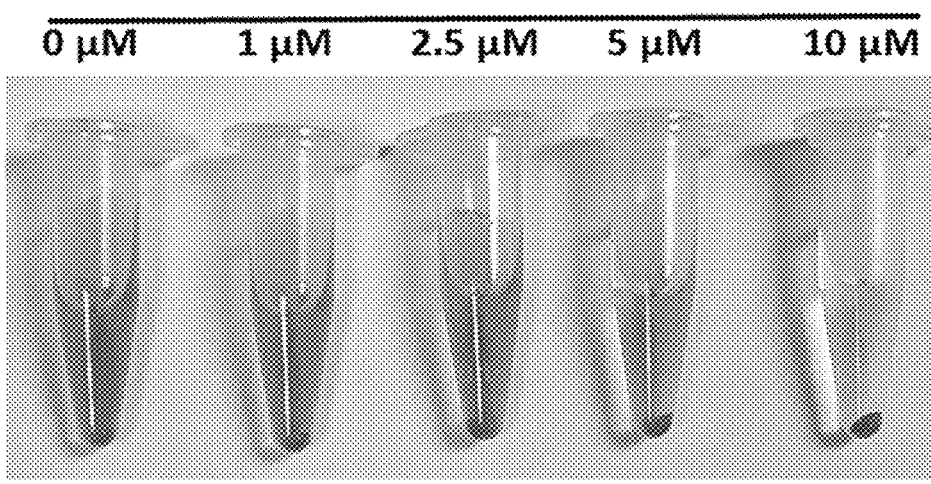
FIG. 5A depicts Myr-CPAMC peptide protecting red blood cells (RBC) from melittin-induced hemolysis.
Figure 5B:
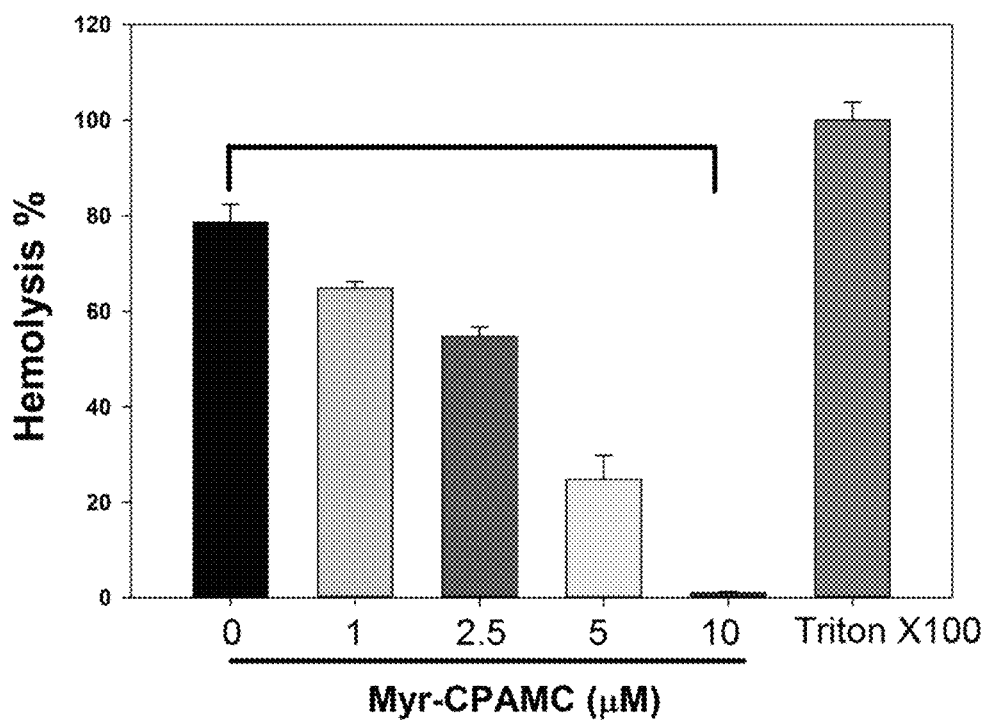
FIG. 5B depicts hemolytic activity of melittin in the presence of Triton-X 100 or increasing concentrations of Myr-CPAMC peptide.

The protective effect of Myr-CPAMC peptide of human red blood cells (RBC) from melittin-induced hemolysis was also examined. To 0.3 mL of 2% human RBC suspension was added to melittin and/or peptide taken in 0.7 mL of PBS. The tubes were incubated at room temperature for 30 min, centrifuged (FIG. 5A) and the OD of the supernatant was measured at 540 nm. PBS and PBS containing 0.1% TritonX-100 served as negative and positive control, respectively. The percentage of hemolysis decreases as Myr-CPAMC concentration increases (FIG. 5B), indicating that Myr-CPAMC peptide also protects human red blood cells (RBC) from melittin-induced hemolysis.

Figure 6A:
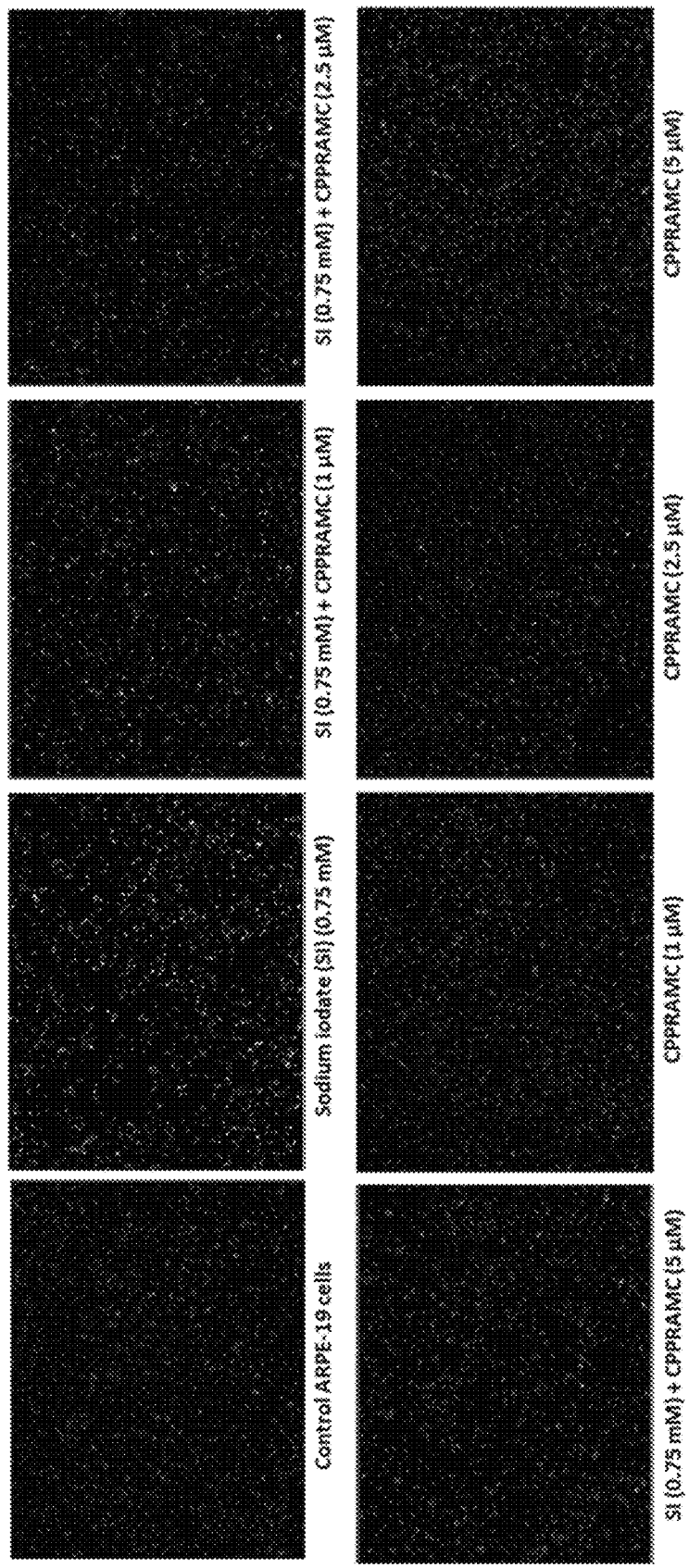
FIG. 6A depicts cell viability imaging of ARPE-19 cells in the presence of sodium iodate and/or CPPRAMC peptide.

Example 3: Blocking of Cytotoxic Action and Oxidative Stress of Sodium Iodate with Peptide Sodium iodate is a chemical that induces oxidative stress and cell death. The ability of CPPRAMC peptide to block the cytotoxic action of sodium iodate was investigated. ARPE-19 cells cultured on a 96-well plate were treated with 7.5 mM sodium iodate and/or CPPRAMC peptide for 24 hours. At the end of the incubation, cell viability imaging was done using the EarlyTox cell integrity kit (Molecular Devices, Sunnyvale, Calif.) (FIG. 6A). The percentage of dead cells in each sample was calculated from the live/dead cell imaging data using the Softmax Pro software (FIG. 6B). CPPRAMC peptide blocks the cytotoxic action of sodium iodate on ARPE-19 cells as shown by cell viability imaging, as the percentage of dead cells in the presence of sodium iodate decreases as the concentration of CPPRAMC increases (FIG. 6B).

The ability of CPPRAMC and CPAMC to suppress sodium iodate-induced oxidative stress in ARPE-19 cells was also assessed. ARPE-19 cells seeded on a 96-well plate were treated with 7.5 mM of sodium iodate and peptides in 100 μl of serum-free DMEM/F12 media for 24 hrs. The cells were then stained with 10 μM DCFH-DA for 30 min at 37° C. in the dark and the cells were observed under the EVOS FL Auto2 imaging system (Thermo Fisher Scientific, Waltham, Mass., USA) with 10× magnification. CPPRAMC and CPAMC were found to reduce or block the oxidative stress induced by sodium iodate as measured by DCFH-DA staining (FIG. 6C).

Figure 7A:
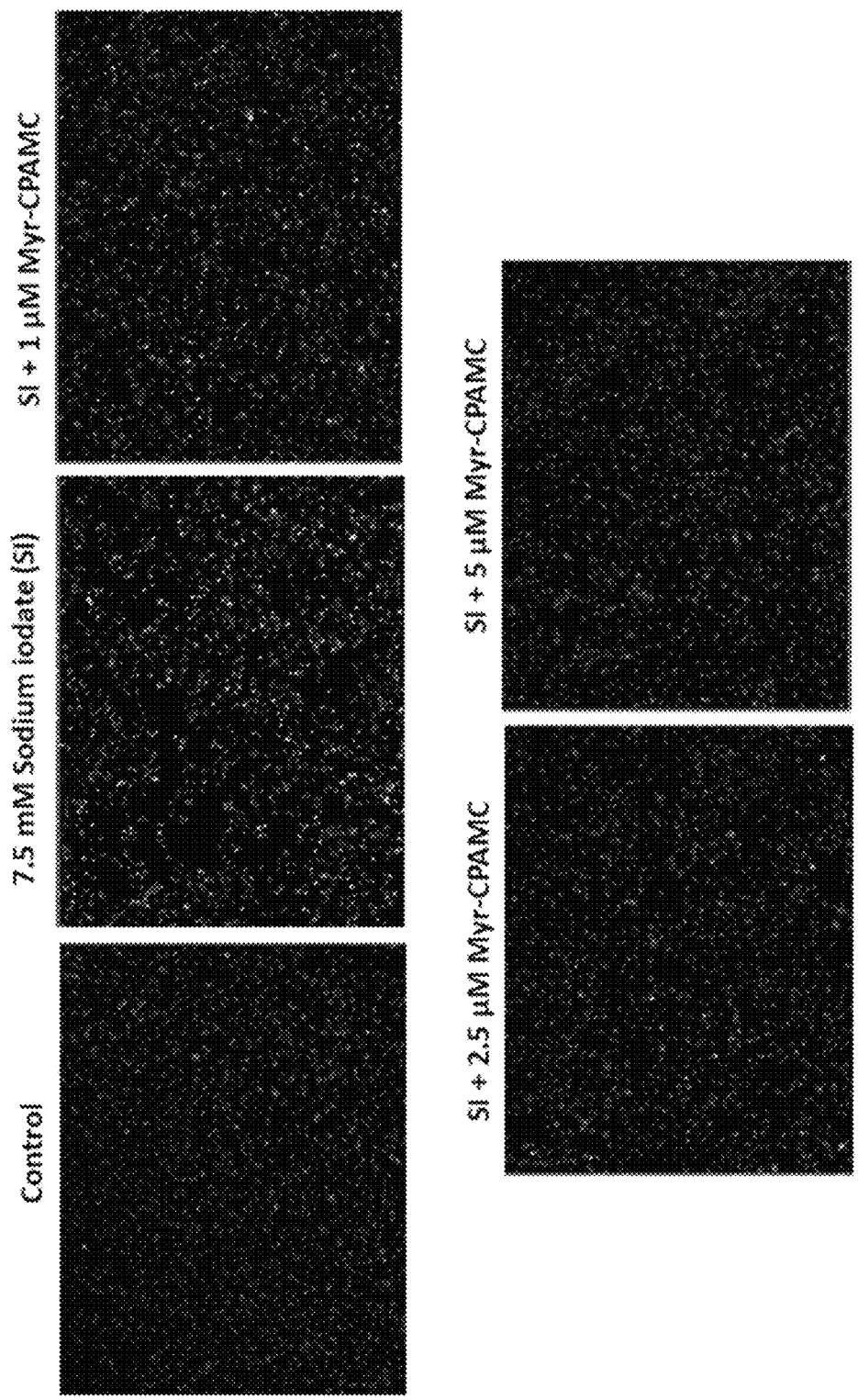
FIG. 7A depicts cell viability imaging of ARPE-19 cells after sodium iodate treatment in the presence of Myr-CPAMC.
Figure 7B:
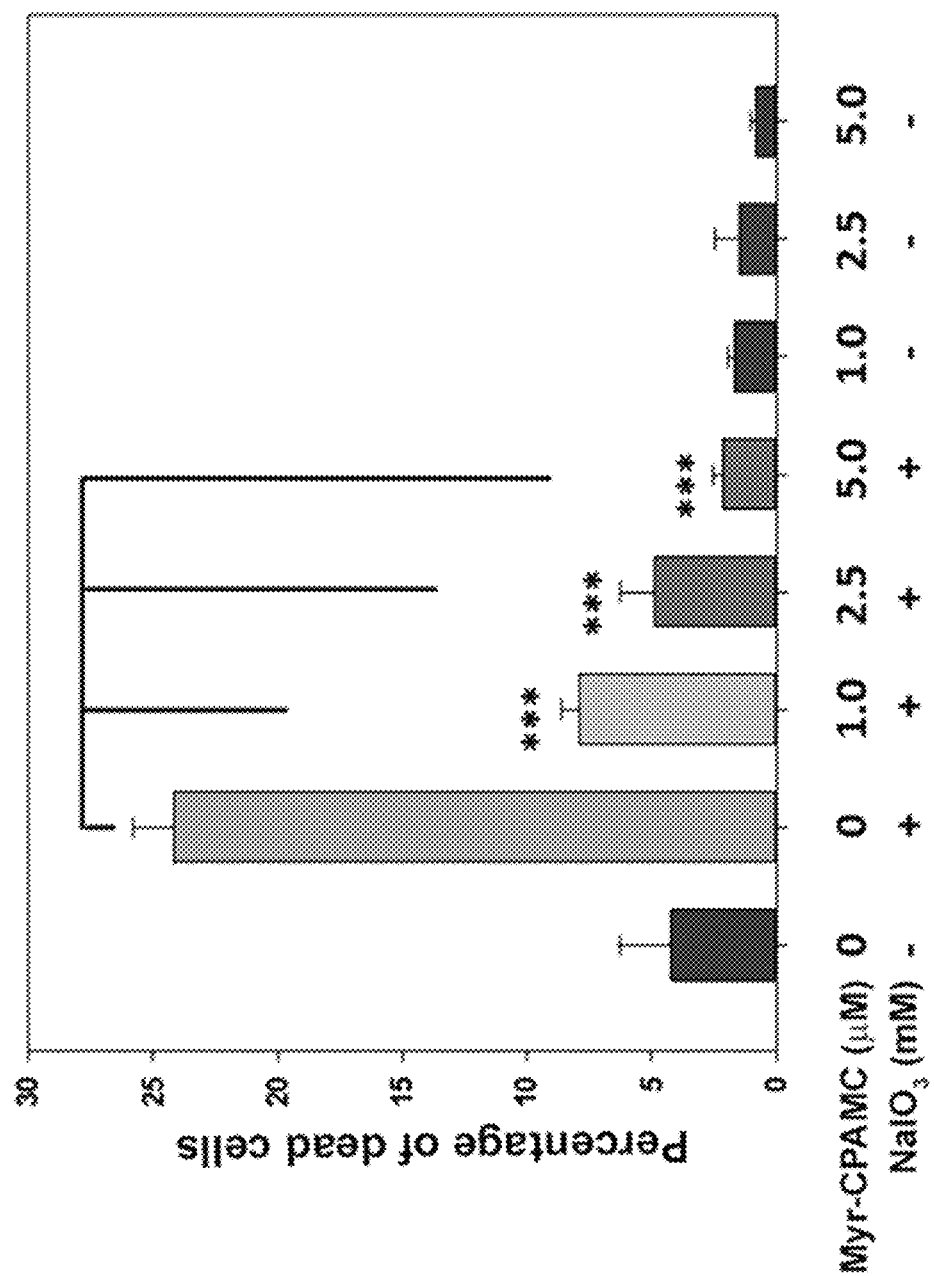
FIG. 7B depicts the effect of Myr-CPAMC on ARPE-19 cell viability in response to sodium iodate oxidative stress. The data shown is an average of six analyses performed on images captured from different wells. *** indicates p-value<0.005.

The ability of Myr-CPAMC peptide to block the cytotoxic action of sodium iodate was also investigated. Authenticated ARPE-19 cells cultured on a 96-well plate were treated with 7.5 mM sodium iodate and/or Myr-CPAMC peptide for 24 hours. At the end of the incubation, cell viability imaging was done using the EarlyTox cell integrity kit (Molecular Devices, Sunnyvale, Calif.) (FIG. 7A). The percentage of dead cells in each sample was calculated from the live/dead cell imaging data using the Softmax Pro software (FIG. 7B). Thus, Myr-CPAMC also protects ARPE-19 cells from sodium iodate-induced cytotoxicity, as the percentage of dead cells in the presence of sodium iodate decreased as Myr-CPAMC concentration increased (FIG. 7B).

Example 4: Blocking of Cytotoxic Action of $A\beta_{1-42}$ with Peptide

Figure 8A:
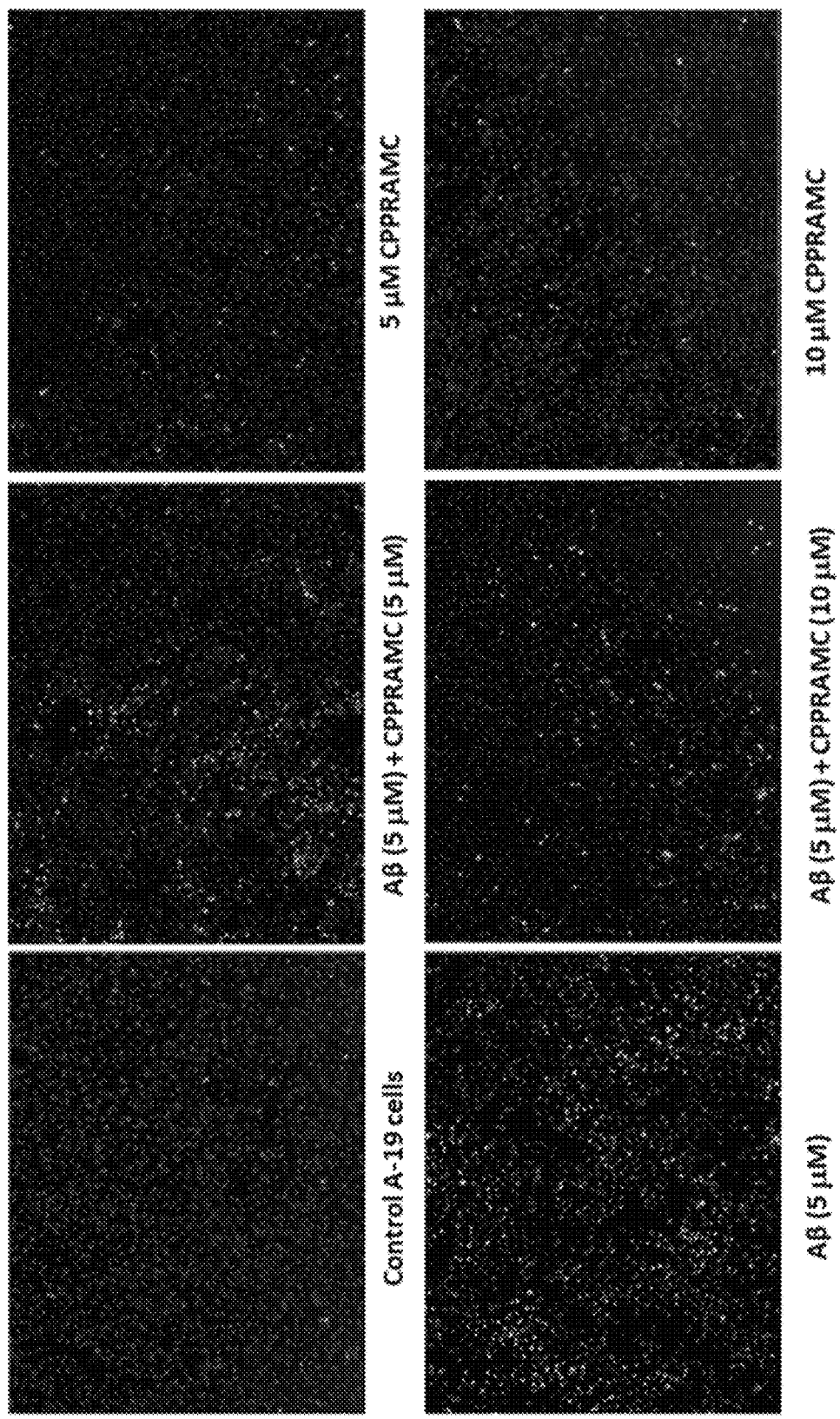
FIG. 8A depicts cell viability imaging of ARPE-19 cells with and without CPPRAMC peptide after $A\beta_{1-42}$-induced cytotoxicity.
Figure 8B:
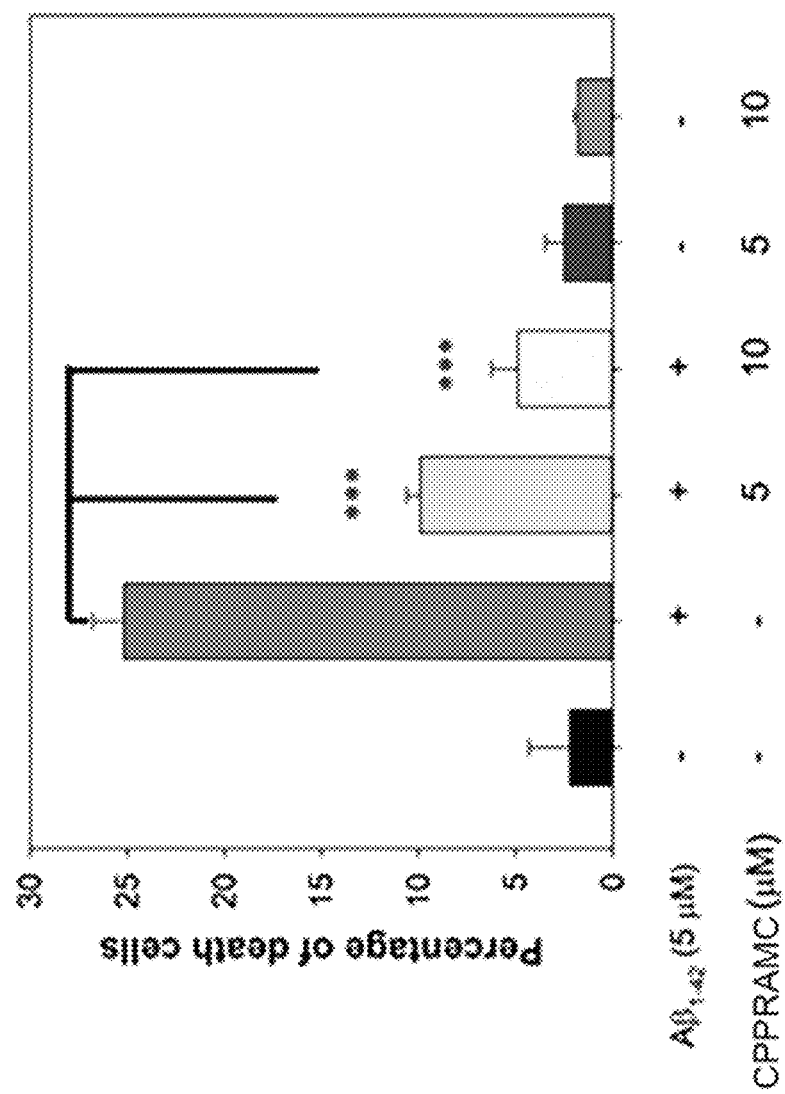
FIG. 8B depicts a quantification of the cell viability imaging data exemplified in FIG. 8A. The data shown is an average of six analyses performed on images captured from different wells. *** indicates P<0.005.

The ability of CPPRAMC peptide to protect against $A\beta_{1-42}$-induced cytotoxicity was also investigated. $A\beta_{1-42}$ and CPPRAMC peptides (1:1 and 1:2) were incubated at 37° C. for 2 hours and treated to ARPE-19 cells cultured on a 96-well plate. After 24 hours, the plate was imaged after staining with EarlyTox cell integrity kit (Molecular Devices, Sunnyvale, Calif.) (FIG. 8A). Cell viability data is graphed, and the percentage of dead cells decreases as a higher concentration of CPPRAMC is added (FIG. 8B), indicating that CPPRAMC peptide protects the ARPE-19 cells from $A\beta_{1-42}$-induced cytotoxicity.

Figure 8C:
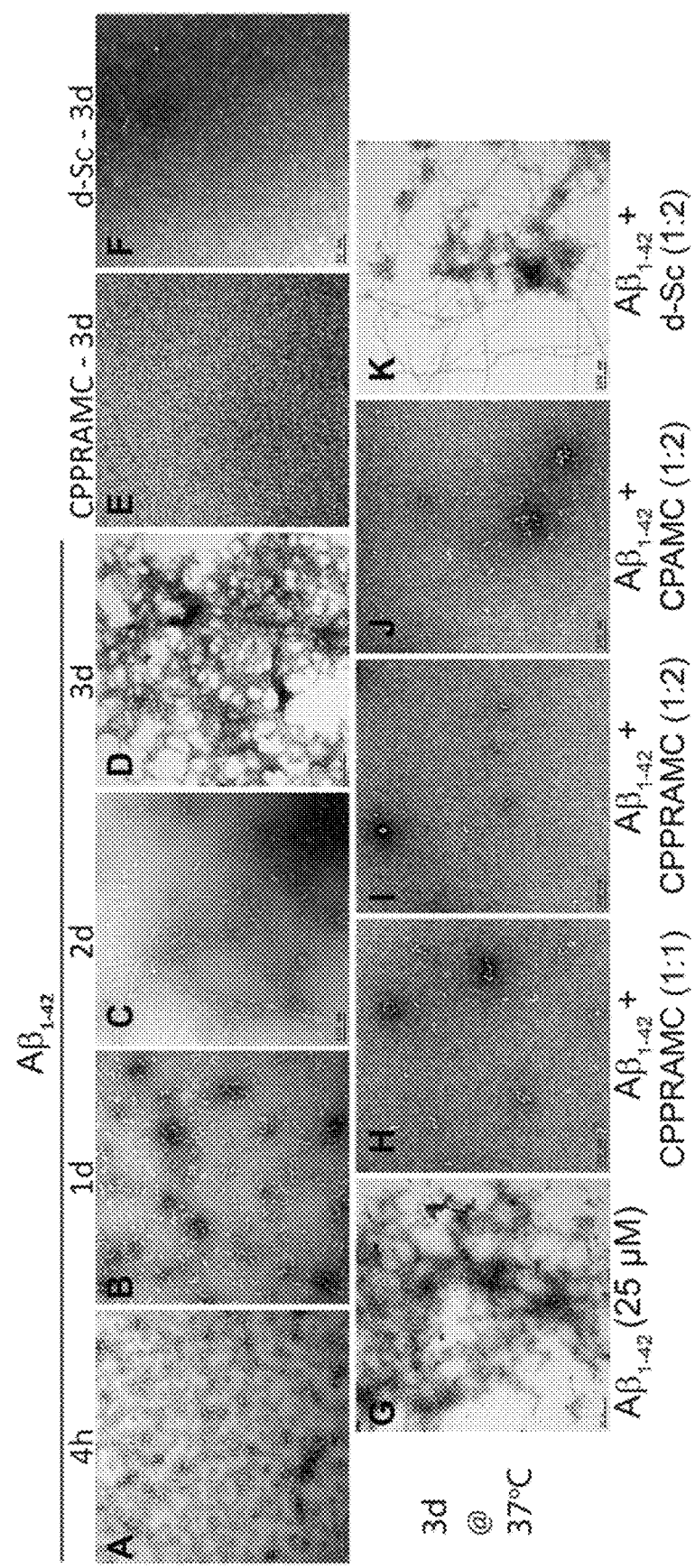
FIG. 8C depicts Aβ$_{1-42}$ oligomerization and fibrillization in vitro with and without CPPRAMC peptide. This shows TEM images of human Aβ$_{1-42}$ and peptide incubations. From left to right in the top row, the first four images were taken of HFIP-treated Aβ$_{1-42}$ (25 μM) incubations in PBS at 37° C. taken at different time points (4 hours to 3 days). From left to right in the top row, the fifth image were taken with CPPRAMC (25 μM) incubated at 37° C. for 3 days. From left to right in the top row, the sixth image taken with d-SC after 3 days of incubation. The bottom row depicts images taken with Aβ$_{1-42}$ incubated without or with peptides for 3 days.

The ability of the CPPRAMC to inhibit β-amyloid fibril formation was tested by incubating the chaperone peptide and human $A\beta_{1-42}$ peptide at 37° C. in PBS (pH 7.4) containing 0.4% $NaN_3$ for up to three days. The incubation mixtures were processed for TEM, and the images were captured (FIG. 8C). The images show that CPPRAMC blocks $A\beta_{1-42}$ oligomerization and fibrillization in vitro (FIG. 8C).

Example 5: Peptides are not Toxic to Cells

Cell viability imaging was performed on cells with increasing concentrations of Myr-CPAMC, with fluorescent staining used to indicate dead cells (FIG. 9A). Myr-CPAMC was shown to be non-toxic to cells.

Figure 9B:
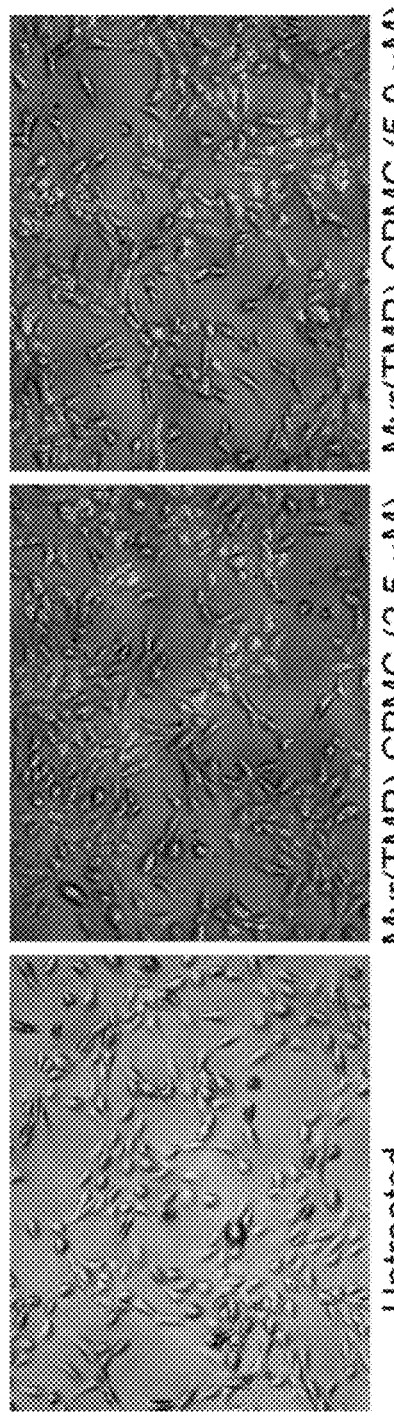
FIG. 9B depicts entry of Myr(TMR)-CPAMC peptide into ARPE-19 cells at different concentrations. Fluorescent stain indicates Myr(TMR)-CPAMC.
Figure 9C:
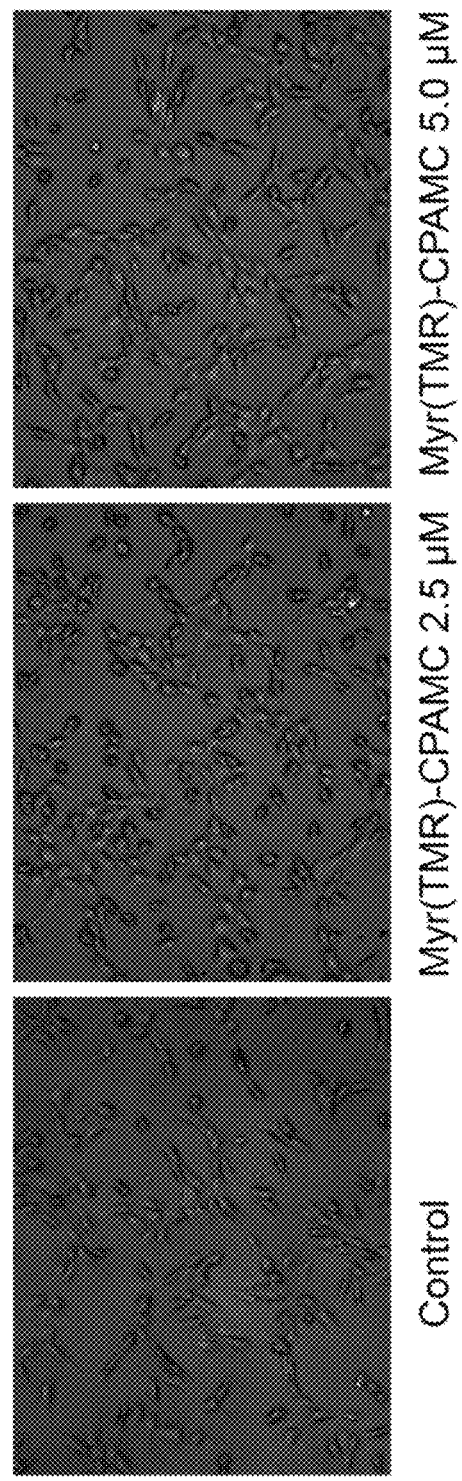
FIG. 9C depicts the effect of Myr(TMR)-CPAMC peptide on cell viability. Fluorescent staining was used to indicate Myr(TMR)CPAMC and living and dead cells.

Fluorescent staining indicating Myr(TMR)-CPAMC demonstrates that Myr-(TMR)-CPAMC peptide can enter into ARPE-19 cells at different concentrations (FIG. 9B). Myr-(TMR)-CPAMC peptide was also shown to be not toxic to cells, as shown by cell viability imaging in the presence of increasing concentrations of Myr(TMR)-CPAMC (FIG. 9C).

Example 6: N2 Lifespan at 20° C. with Peptide

Figure 10A:
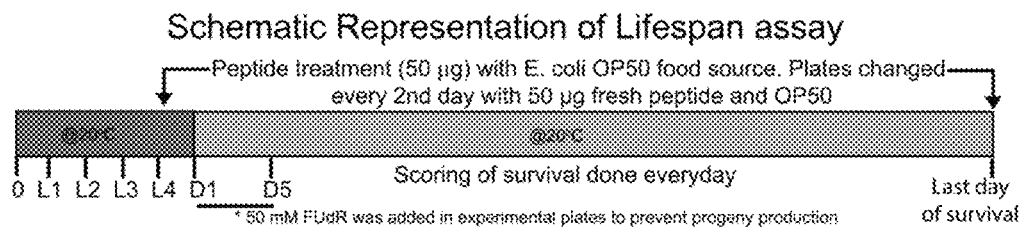
FIG. 10A depicts a schematic representation of lifespan assay used to determine how CPPRAMC feeding augments the lifespan of wild-type *C. elegans*.

A schematic of an assay of C. elegans N2 lifespan at 20° C. is shown (FIG. 10A). This involved peptide treatment (50 μg) with E. coli OP50 as a food source. Plates were changed every second day with 50 μg fresh peptide and OP50. Scoring of survival was done every day to the last day of survival. 50 mM FUdR was added in experimental plates between D1 and D5 to prevent progeny production.

Figure 10B:
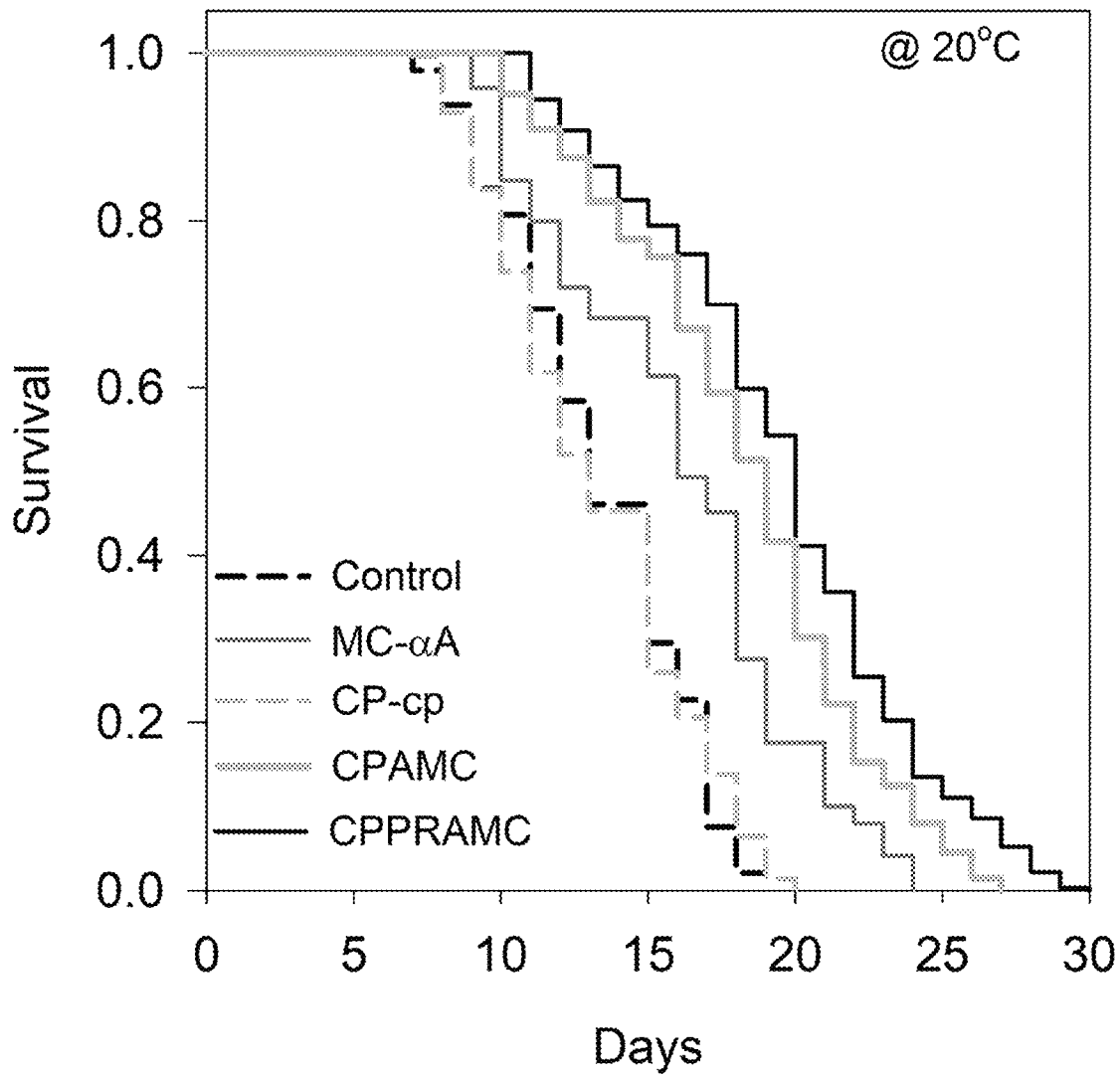
FIG. 10B depicts the Kaplan-Meier Survival Analysis after conducting the experiment outlined in FIG. 10A. The survival analysis was done using Kaplan-Meier survival log-rank test followed by Holm-Sidak method in Sigma-PlotV 12.5. A summary of this analysis is shown in Table 2.

The Kaplan-Meier survival analysis shows that worms treated with the amphiphilic peptide chaperones survive longer than the control (FIG. 10B). A summary of the analysis is shown in Table 2.

TABLE 2

Summary of Kaplan-Meier Survival Analysis
The survival analysis was done using Kaplan-Meier survival log-rank test followed by Holm-Sidak method in SigmaPlotV 12.5.

| Treatments | Median Lifespan (Days ± SE) | Sample size (N) | Increase in median survival (%) |
|---|---|---|---|
| Control | 13.38 ± 0.19 | 271 | |
| CPPRAMC | 19.57 ± 0.25 | 270 | 46* |
| CPAMC | 18.23 ± 0.25 | 290 | 36* |
| MC-αA | 16.10 ± 0.25 | 270 | 20* |
| CP-cp | 13.23 ± 0.20 | 276 | 0 |

*Indicates a p-value < 0.0001.

Example 7: N2 Lifespan at 35° C. with Peptide

The lifespan of wild type C. elegans with and without peptide at a restrictive temperature was measured.

Figure 11A:
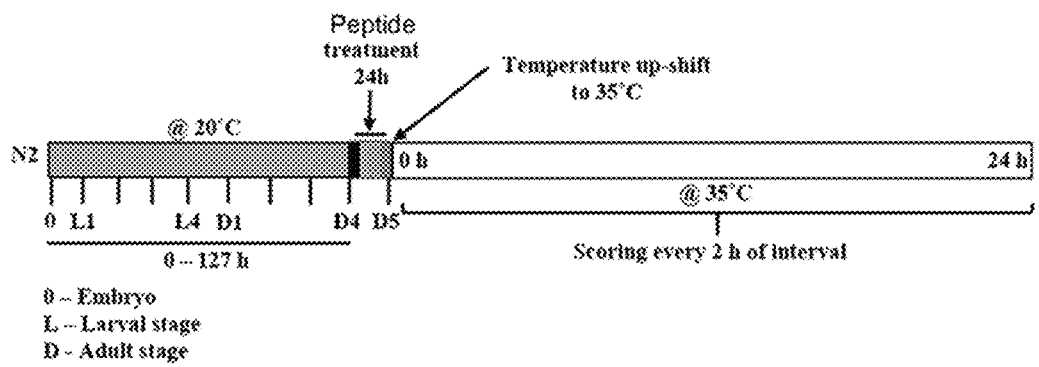
FIG. 11A depicts a schematic representation of the thermotolerance assay used to test the ability of peptides to protect *C. elegans* (N2 strain) against thermal induced stress.
Figure 11B:
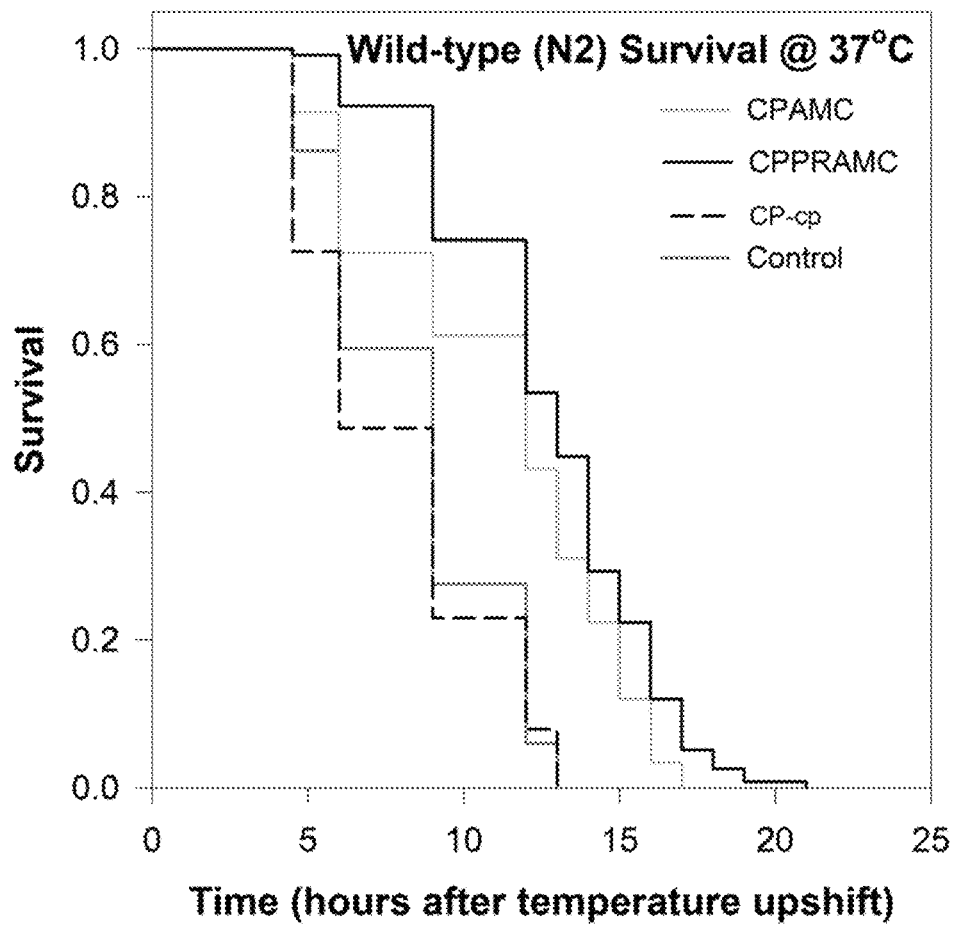
FIG. 11B depicts a Kaplan-Meier Survival Analysis of the results of the thermotolerance assay depicted in FIG. 11A. The survival function is estimated by the Kaplan-Meier method with a summary of this analysis shown in Table 3.

A schematic representation of the thermotolerance assay used is shown (FIG. 11A). 24 hours of 50 μg peptide treatment at 20° C. of a synchronized population of wild type C. elegans was followed by a continuous heat stress at 35° C. Worms were scored every two hours for 24 hours for survival. The results show how CPPRAMC and CPAMC peptide protects C. elegans (N2 strain) against thermal induced stress (FIG. 11B). A summary of this analysis is shown in Table 3.

TABLE 3

Summary of Kaplan-Meier Survival Analysis
Data is presented as Mean ± SE. Significance levels were calculated using the Holm-Sidak method.

| Treatments | Median survival ± SE (hours at 35° C.) | Sample size (N) | % Increase in survival |
|---|---|---|---|
| Control | 8.4 ± 0.2 | 109 | |
| CPPRAMC - 50 μg | 12.7 ± 0.3 | 108 | 51* |
| CPAMC - 50 μg | 11.0 ± 0.4 | 113 | 31* |
| CP-cp - 50 μg | 7.4 ± 0.4 | 119 | 0 |

*** indicates a p-value < 0.001.

Example 8: CL2006 Lifespan at 20° C. with Peptide

CL2006 C. elegans were used as a paralysis and death model. Worms are maintained at 15° C., with adult onset paralysis induced at 20° C.

Figure 12:
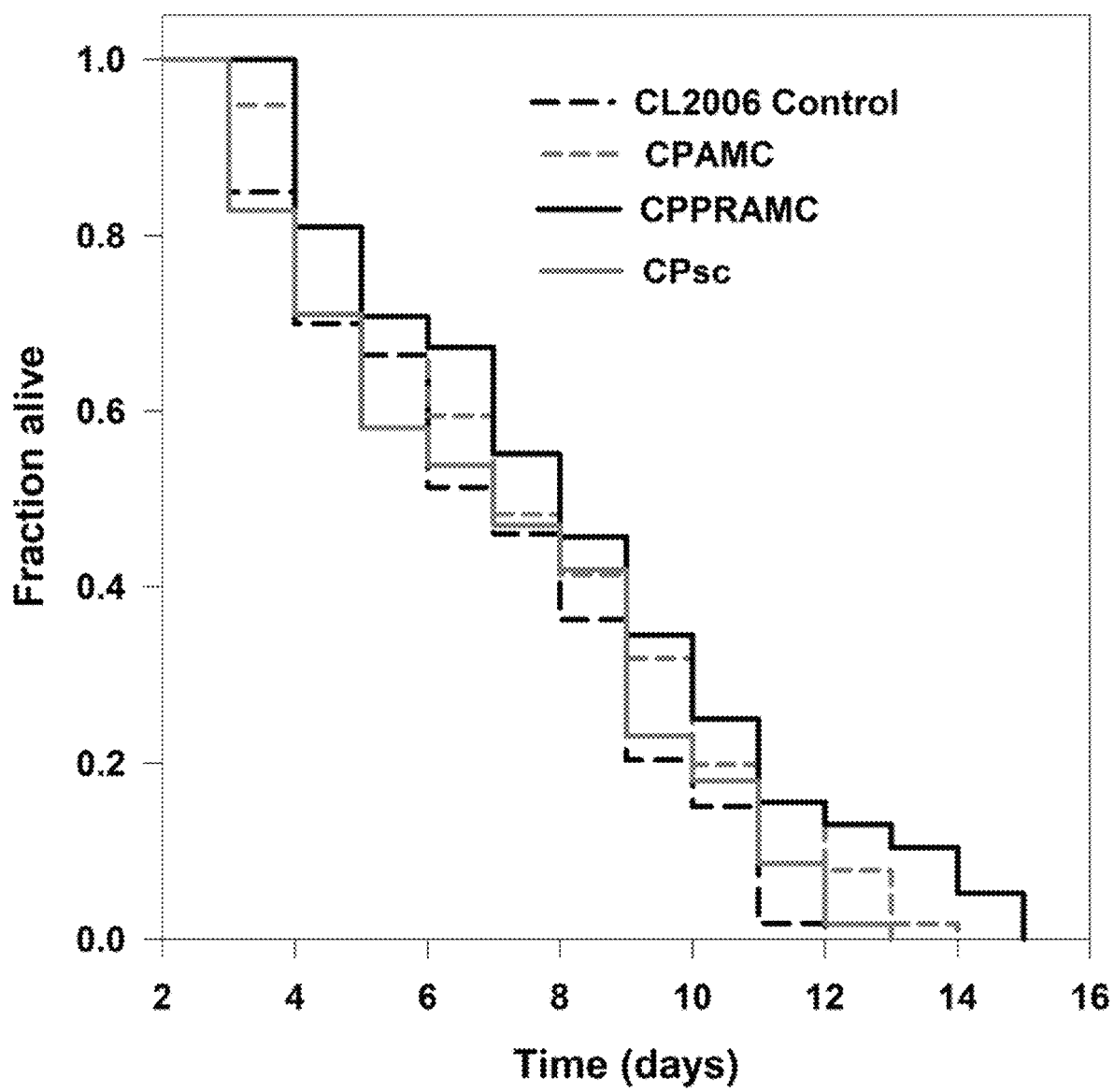
FIG. 12 depicts a Kaplan-Meier Survival Analysis of the results of CL2006 worms with and without peptide treatment. A summary of the Kaplan-Meier survival analysis is shown in Tables 9-10.

50 μg CPAMC and CPPRAMC peptide or controls were added to CL2006 worms, and the fraction left alive over time at the restrictive temperature of 20° C. was quantified (FIG. 12). 50 μg peptide treatment was able to significantly enhance survival of CL2006 at 20° C. (FIG. 12). A summary of Kaplan-Meier survival analysis is shown in Tables 4-5.

TABLE 4

Summary of Kaplan-Meier Survival Analysis

| Treatment (50 μg) | Median survival ± SE (days at 20° C.) | Sample size (N) | % increase in survival |
|---|---|---|---|
| Control | 6.9 ± 0.26 | 113 | |
| CPAMC | 7.7 ± 0.28 | 116 | 11.6 |
| CPPRAMC | 8.2 ± 0.30 | 116 | 19.1 |
| CP-sc | 7.0 ± 0.28 | 117 | 2.0 |

TABLE 5

Probabilities associated with Table 4. Significance levels were calculated using the Holm-Sidak method.

| Comparison | p-Value | Significant? |
|---|---|---|
| Control vs. CPPRAMC | 0.00422 | Yes |
| CPPRAMC vs. CP-sc | 0.0195 | Yes |
| Control vs. CPAMC | 0.0449 | Yes |
| CPAMC vs. CP-sc | 0.208 | No |
| CPAMC vs. CPPRAMC | 0.178 | No |
| Control vs. CP-sc | 0.299 | No |

Example 9: Peptide Increases Survival and Prevents Paralysis in Paralysis and Alzheimer's Disease Models CL4176 C. elegans is a temperature sensitive strain. Worms are maintained at 15° C. and shifted to increased temperature to cause Aβ-induced paralysis in adults. This has been used as a C. elegans model of Alzheimer's disease.

Figure 13A:
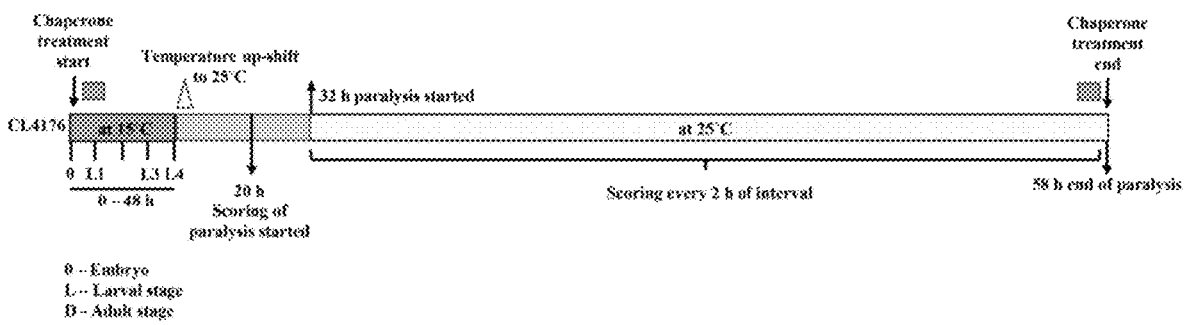
FIG. 13A depicts a schematic representation of a paralysis assay used to test the ability of peptides to delay Aβ-induced paralysis in CL4176 worms.

A scheme of a paralysis assay with CL4176 worms is shown (FIG. 13A). Peptide treatment began on CL4176 embryos and continued throughout the experiment. After 2 days at 15° C., the temperature was increased to the restrictive temperature of 25° C. Worms were scored for survival and paralysis.

Figure 13B:
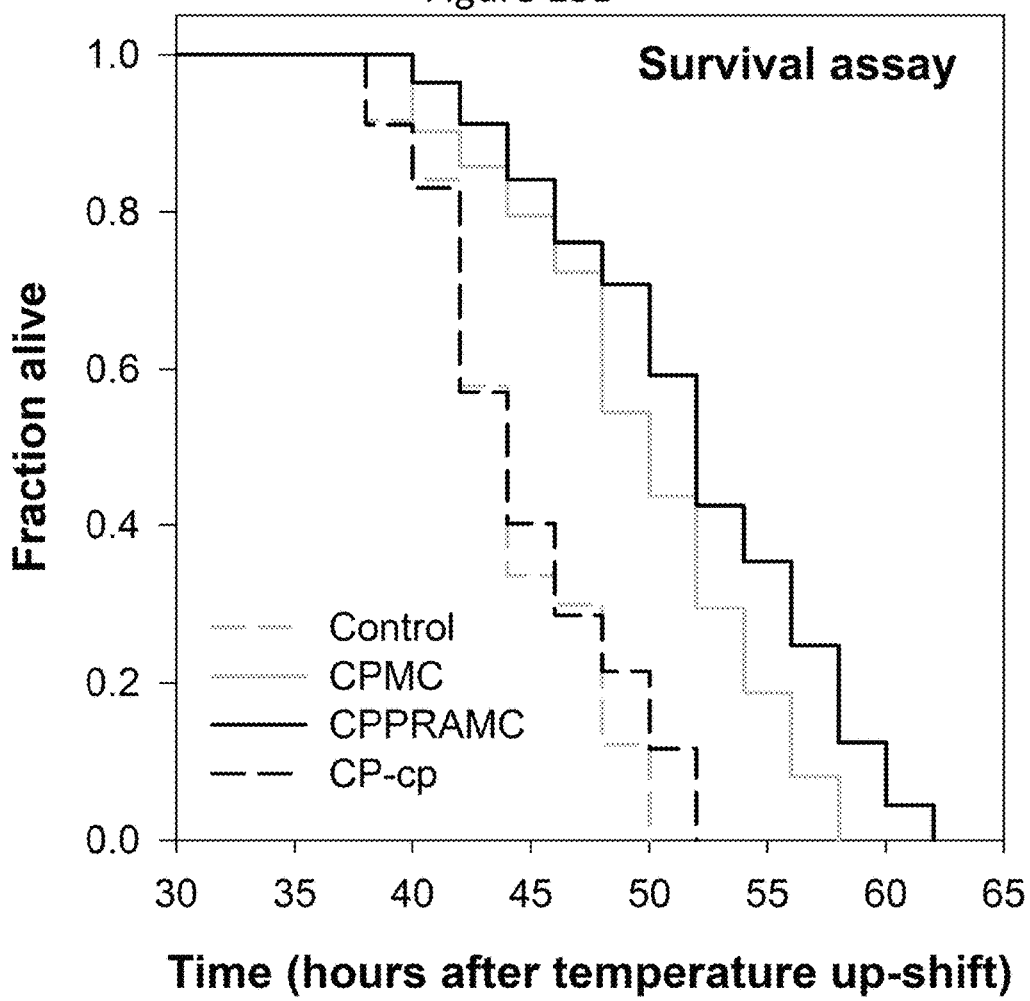
FIG. 13B depicts a Kaplan-Meier Survival Analysis of the results of the assay depicted in FIG. 13A. A table depicting a summary of the survival analysis of CL4176 is shown in Table 6.

A Kaplan-Meier Survival Analysis demonstrates how CPPRAMC and CPAMC increase survivability in CL4176 worms (FIG. 13B). A table depicting a summary of the survival analysis of CL4176 is shown in Table 6.

TABLE 6

Summary of Survival Analysis of CL4176

| Group | Median survival Hours ± SE | % increase in median survival |
|---|---|---|
| Control | 44.2 ± 0.3 | |
| CPPRMC | 51.9 ± 0.6* | 18 |
| CPAMC | 49.6 ± 0.5* | 12 |
| CP-cp | 44.7 ± 0.4 | 0 |

*indicates p-value < 0.001 compared to control (untreated).

Figure 13C:
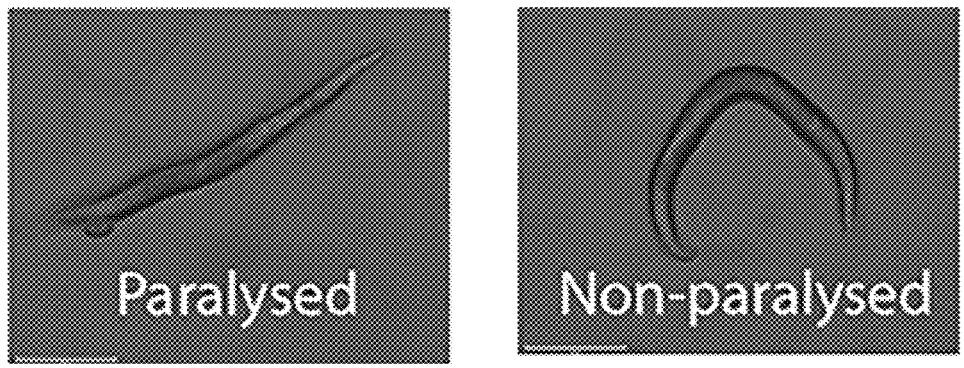
FIG. 13C depicts an example of a paralyzed and non-paralyzed *C. elegans*.
Figure 13D:
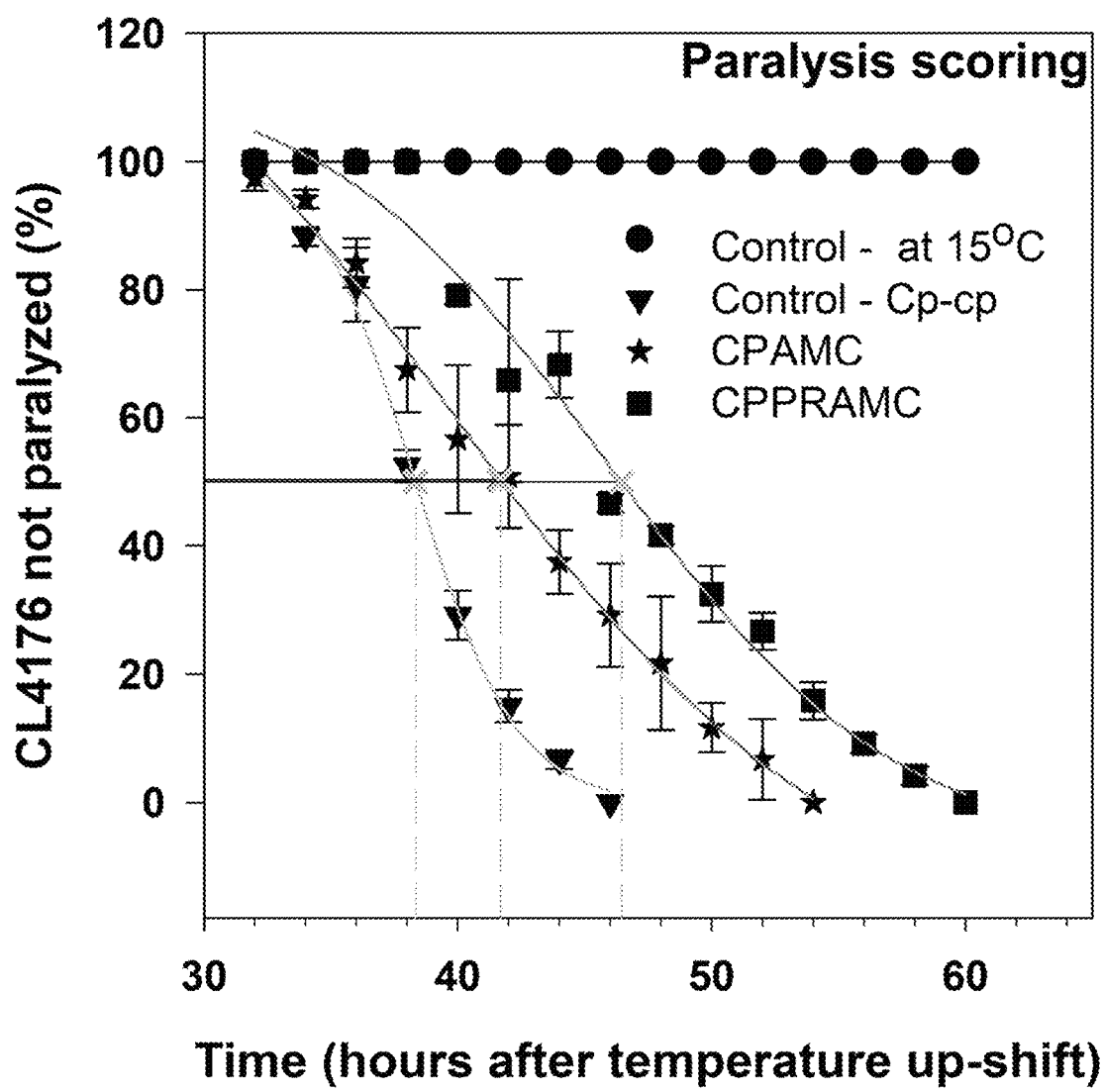
FIG. 13D depicts scoring of Aβ-induced paralysis in CL4176 worms with and without peptide.

Example images of paralyzed and non-paralyzed worms are shown (FIG. 13C). After scoring worms for paralysis, it was found that treatment with CPPRAMC or CPAMC results in a delay of CL4176 worm paralysis compared to controls (FIG. 13D).

Example 10: Peptide Protects Against Induced Oxidative Stress

The ability of these peptides to protect against oxidative stress induced by Paraquat (PQ) or Juglone (JG) was investigated.

Figure 14:
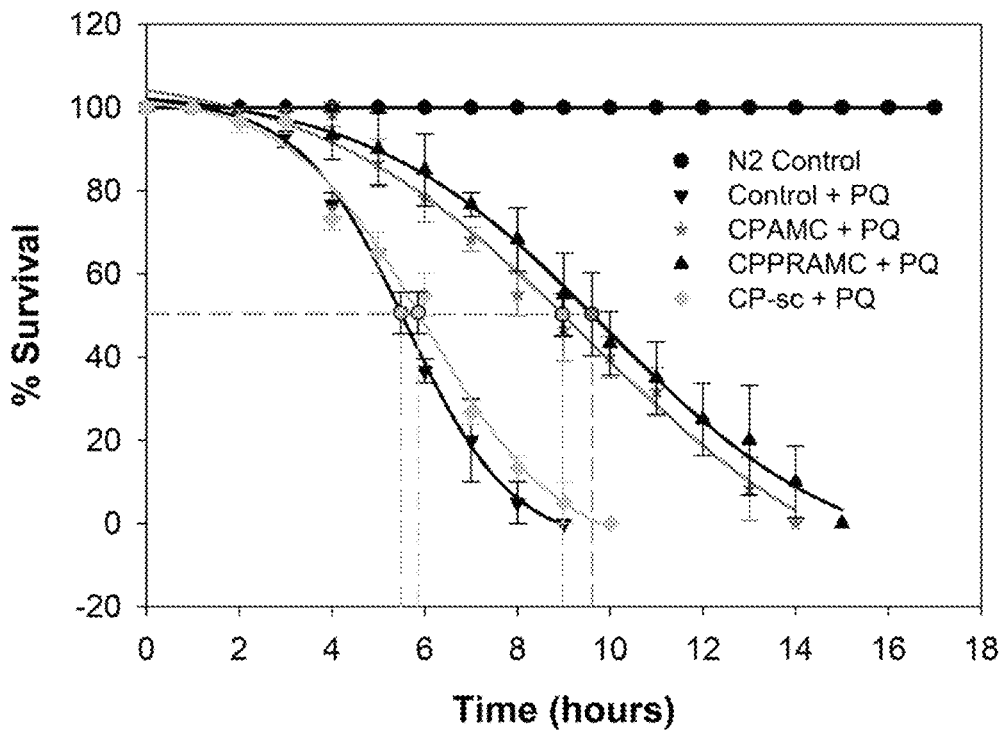
FIG. 14 depicts survival of *C. elegans* wild-type (N2 strain) worms under conditions of paraquat (PQ)-induced oxidative stress with peptide or control treatment. Data were expressed as the percentage of worms survived. The scatter graph was plotted in SigmaPlot version 12.5, followed by a global curve fit wizard.

Five-day old N2 worms were pretreated with 50 μg peptide for 24 hours and subjected to 50 mM PQ. The survival of the worms was monitored every hour under a microscope until the end of survival. Worms that do not show any movement or response while poking were considered dead. The median survival value (50% survival) in CPPRAMC, CPAMC, and CP-SC (control) peptides corresponds to 9.6 h, 8.9 h and 5.9 h, respectively, as compared to vehicle control (5.5 h) (FIG. 14). These results indicate that amphiphilic peptides CPAMC and CPPRAMC protect C. elegans wild-type (N2 strain) against 50 mM paraquat (PQ)-induced oxidative stress.

Figure 15:
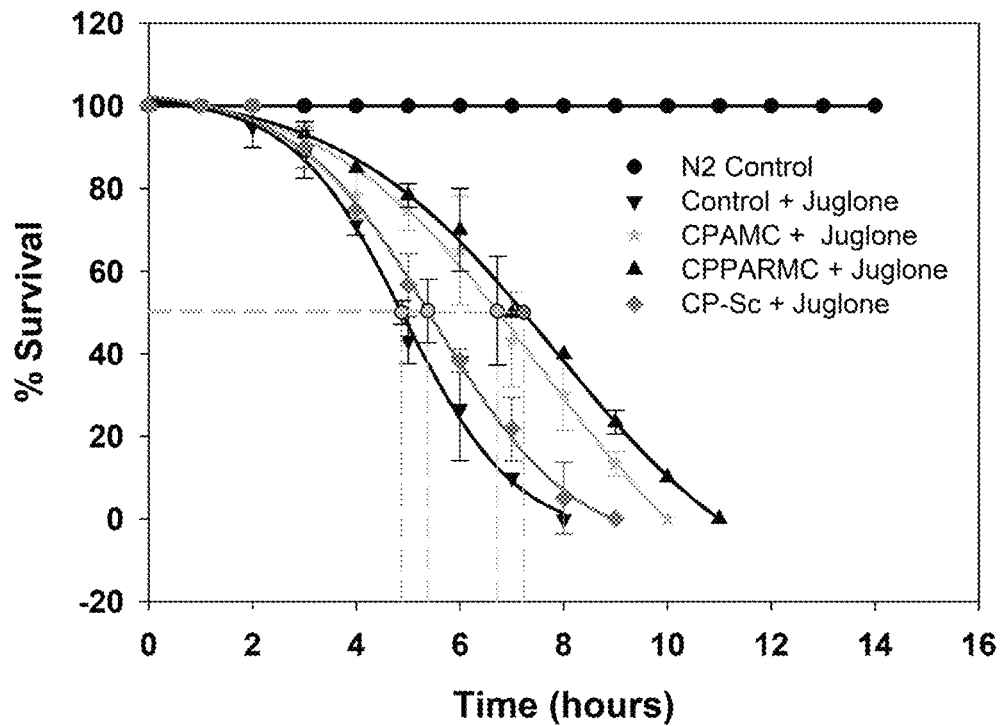
FIG. 15 depicts survival of *C. elegans* (N2) worms under juglone (JG)-induced oxidative stress with peptide or control treatment. Data were expressed as the percentage of worms survived. The scatter graph was plotted in SigmaPlot version 12.5, followed by a global curve fit wizard.

N2 worms at day 5 pretreated for 24 h with 50 μg CPAMC or CP-SC (control) and subjected to 50 μM JG. Survival was checked every hour under a microscope until the end of survival. The median survival value in CPAMC and CP-SC (control) peptides corresponds to 7.3 h and 5.9 h, respectively, compared to vehicle control (4.9 h) (FIG. 15). These results indicate that amphiphilic peptides CPAMC and CPPRAMC protect C. elegans (N2) worms against 50 μM Juglone (JG)-induced oxidative stress.

Example 11: FITC Labeled CPPRAMC Peptide can be Loaded into Exosomes

Figure 16A:
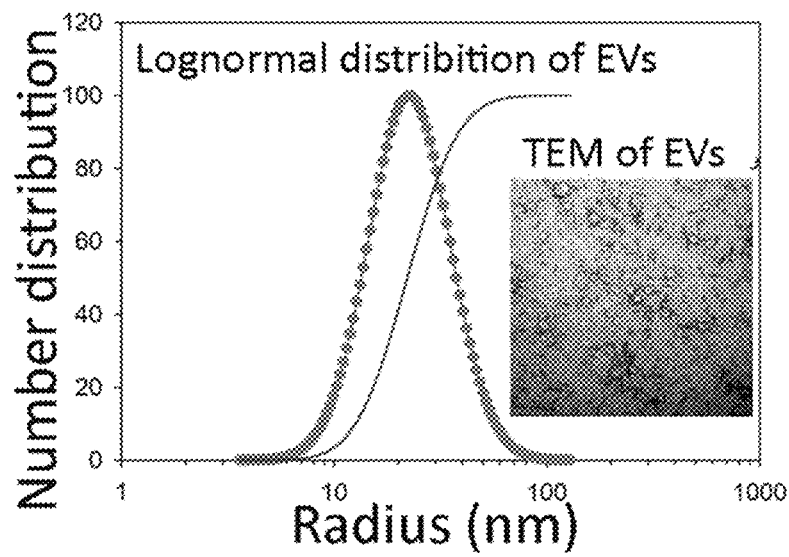
FIG. 16A shows the size of purified extracellular vesicles (EVs) loaded with FITC-labeled CPPRAMC by incubation at 37° C. They were analyzed by dynamic light scattering (DLS) analysis. A TEM image of the loaded EVs is also shown.
Figure 16B:
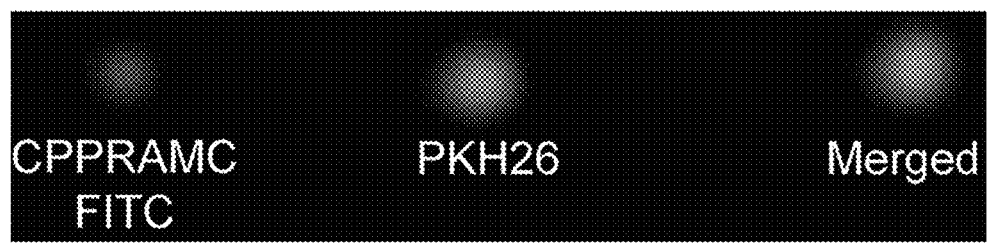
FIG. 16B shows confocal images of FITC-labeled CPPRAMC loaded EVs labeled with PKH26. This was done with a 63× water immersion objective with additional 48X zoom, equivalent to 3024× objective magnification.
Figure 16C:
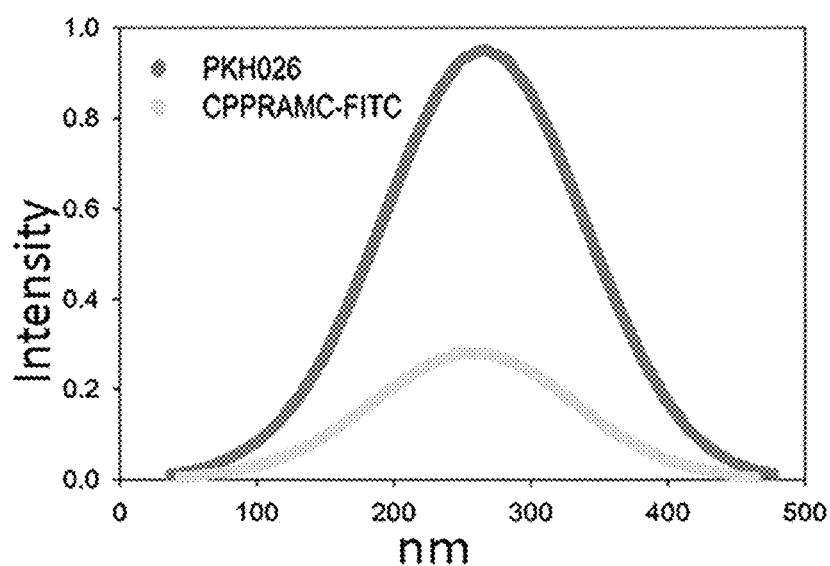
FIG. 16C shows the results of spectral imaging of EV-loaded FITC-labeled CPPRAMC.

FITC-labeled CPPRAMC peptides were loaded onto extracellular vesicles (EVs) by incubation at 37° C. The size of these EVs was quantified by dynamic light scattering analysis (FIG. 16A). Co-localization of the FITC-labeled CPPRAMC and EVs was demonstrated via confocal (FIG. 16B) and spectral (FIG. 16C) imaging, indicating the presence of peptide inside the EVs.

Example 12: Peptide is Resistant to Proteolytic Cleavage

Figure 17:
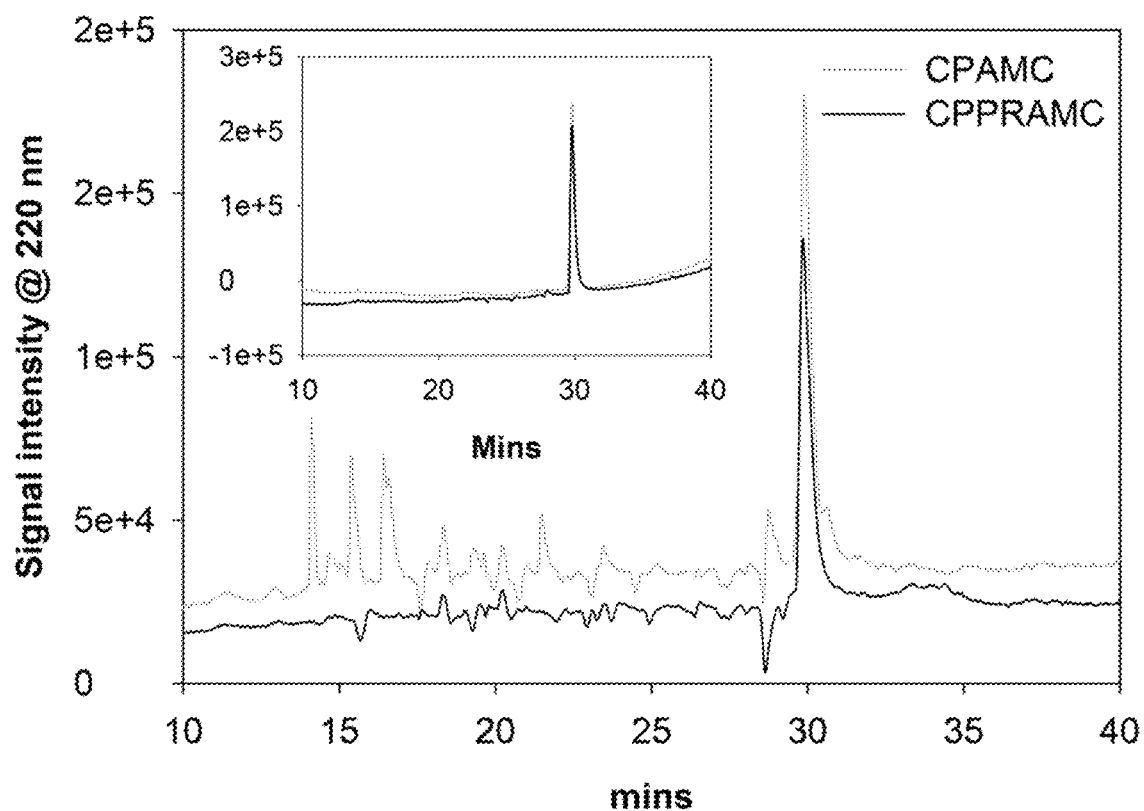
FIG. 17 depicts HPLC profiles of overnight incubations of chaperone peptides (100 μg) with Proteinase K (10 μg). Profile of the sample containing the protease alone was subtracted and plotted.

CPPRAMC is resistant to proteolytic cleavage as shown by HPLC profiles of overnight incubations of chaperone peptides (100 μg) with Proteinase K (10 μg) (FIG. 17).

Example 13: Peptide Readily Penetrates Cells

Figure 18:
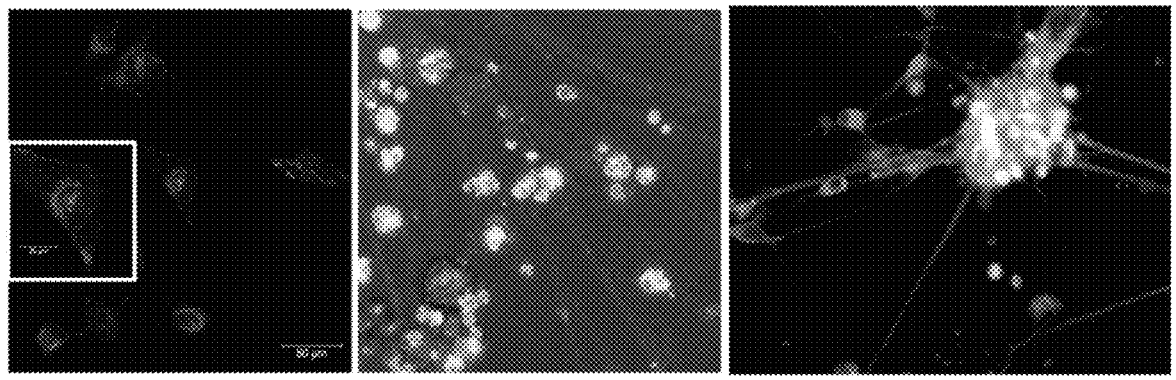
FIG. 18 depicts CPPRAMC penetration of cells. The left image shows ARPE-19 cells treated with FITC labeled CPPRAMC. The middle image shows hiPSC-NSC cultures showing the peptide entry into cells. The right image shows NSC-derived neurons showing the peptide entry.

ARPE-19 cells, hiPSC-NSC cultures, and NSC-derived neurons treated with FITC-labeled CPPRAMC have a signal for the peptide, indicating that CPPRAMC readily penetrates neural cells (FIG. 18).

Example 14: Peptide Suppresses Inflammatory Response

Figure 19A:
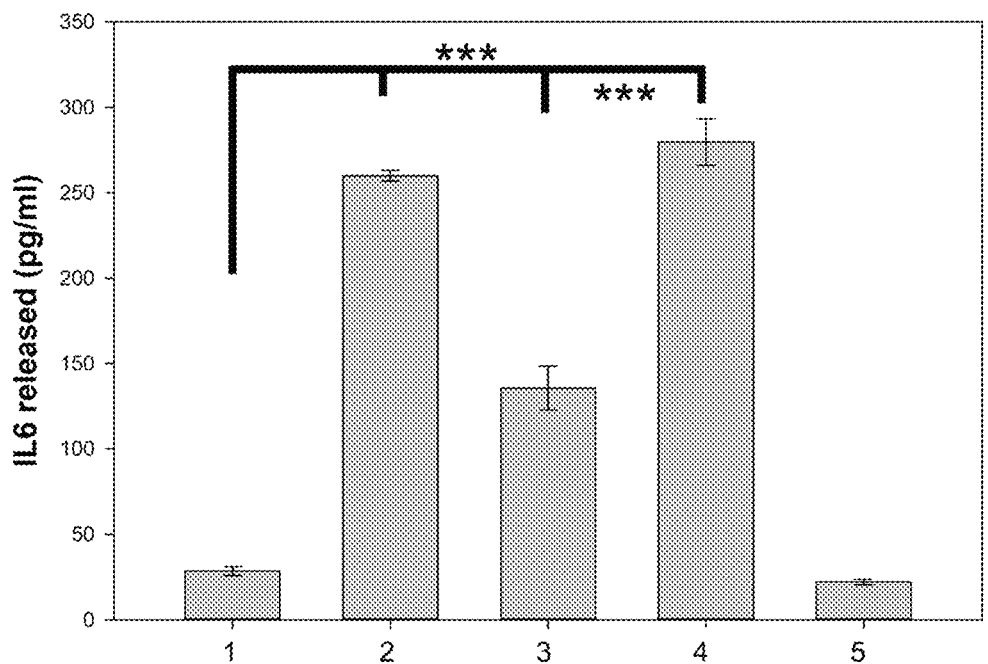
FIG. 19A depicts suppression of LPS-induced inflammatory response in mouse macrophages by CPPRAMC. 1 indicates CPPRAMC (5 μg/mL). 2 indicates CPPRAMC pretreated for 3 h before LPS treatment. 3 indicates CPPRAMC preincubated with LPS for 1 h before treating the cells. 4 indicates LPS alone 1 μg/mL. 5 indicates cell culture media.

Mouse macrophages were treated with CPPRAMC and/or LPS, and IL6 in the cell culture supernatants was measured 24 h after treatment using mouse IL6 DuoSet ELISA (R&D systems) (FIG. 19A). The results indicate that LPS-induced inflammatory response is suppressed in mouse macrophages by CPPRAMC (FIG. 19A).

HEK293 IL-6 reporter cells were treated with human recombinant IL-6 and the peptides for 1 hr. The STAT3-stimulated SEAP activity in the culture supernatant was measured using QUANTI-Blue solution (InvivoGen) (FIG.

Figure 19B:
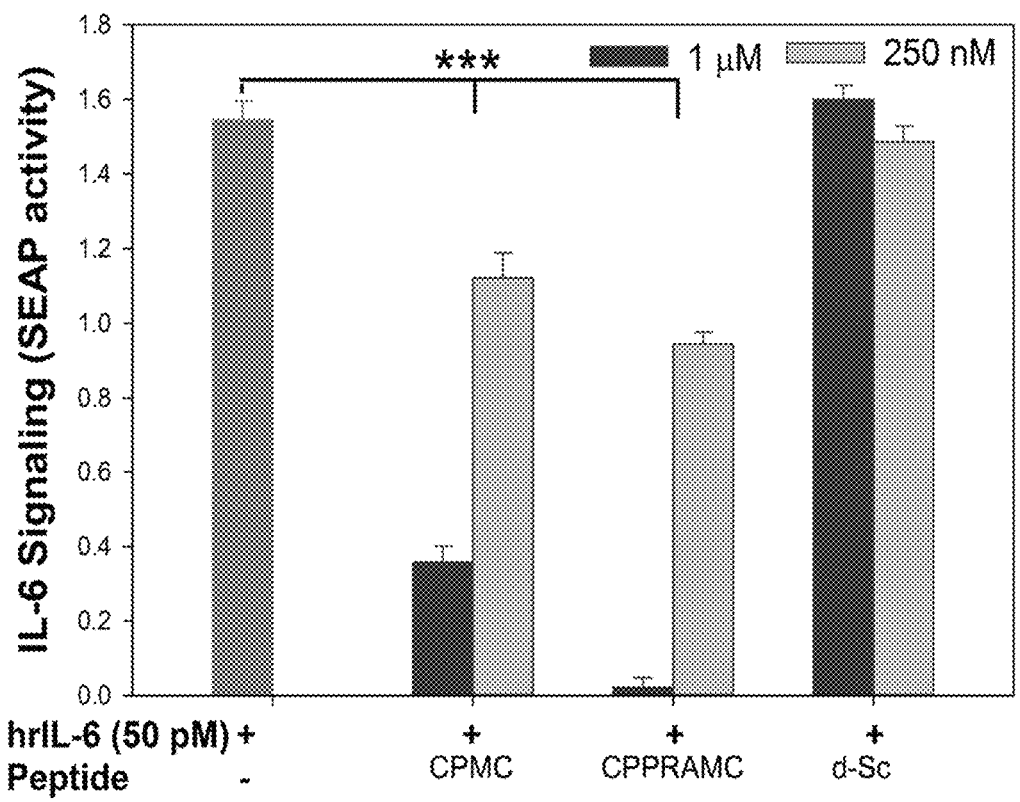
FIG. 19B depicts IL-6 signaling in the presence of hrIL-6 with and without peptide. Data is an average±SD of six wells. * indicates P<0.005.

19B). The results indicate that IL-6 signaling is also suppressed by CPPRAMC and CPMC (FIG. 19B).

Example 15: GFP-fused Peptide can Be Expressed in COS7 Cells

Figure 20A:
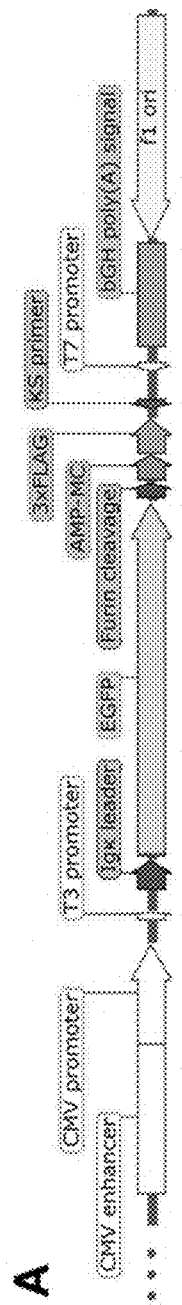
FIG. 20A depicts design of the peptide expression vector for expressing GFP-fused peptide in Cos7 cells.
Figure 20E:
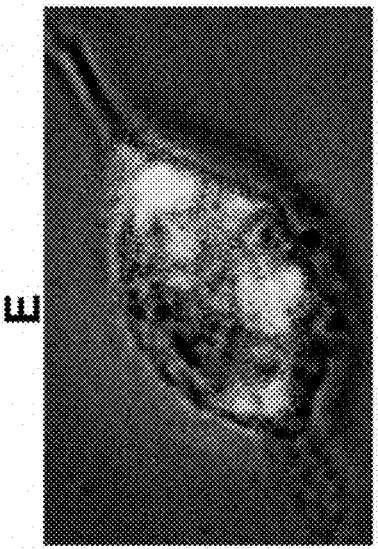
FIG. 20E depicts Cos7 cells expressing non-secretory EGFP-CPAMC.

The design of the peptide expression vector for expressing GFP-fused peptide in Cos7 cells is shown (FIG. 20A). Secretory EGFP-tagged CPAMC was successfully expressed in Cos7 cells (FIG. 20B).

Figure 20D:
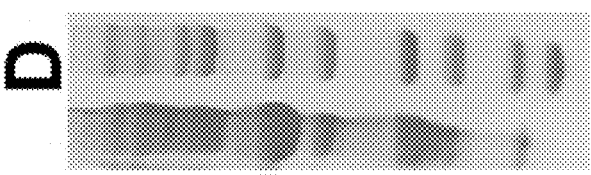
FIG. 20D depicts SDS Page analysis of culture supernatant. Left lane shows the supernatant; right lane shows size markers.
Figure 20C:
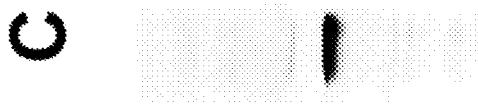
FIG. 20C depicts Western blot analysis of Cos7 culture supernatants expressing secretory proteins probed with anti-GFP antibody.
Figure 20B:
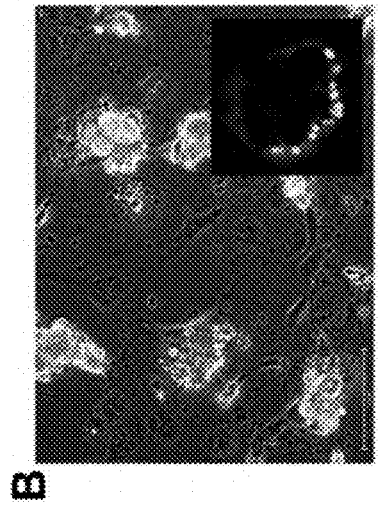
FIG. 20B depicts expression of secretory EGFP-tagged CPAMC.

A Western blot analysis of Cos7 culture supernatants expressing secretory proteins probed with anti-GFP antibody produces a strong band (FIG. 20C), with SDS Page analysis of culture supernatant also shown (FIG. 20D).

Cos7 cells expressing non-secretory EGFP-CPAMC are also shown (FIG. 20E).

Example 16: Ad Deposits are Reduced in Peptide-treated Worms

Figure 21:
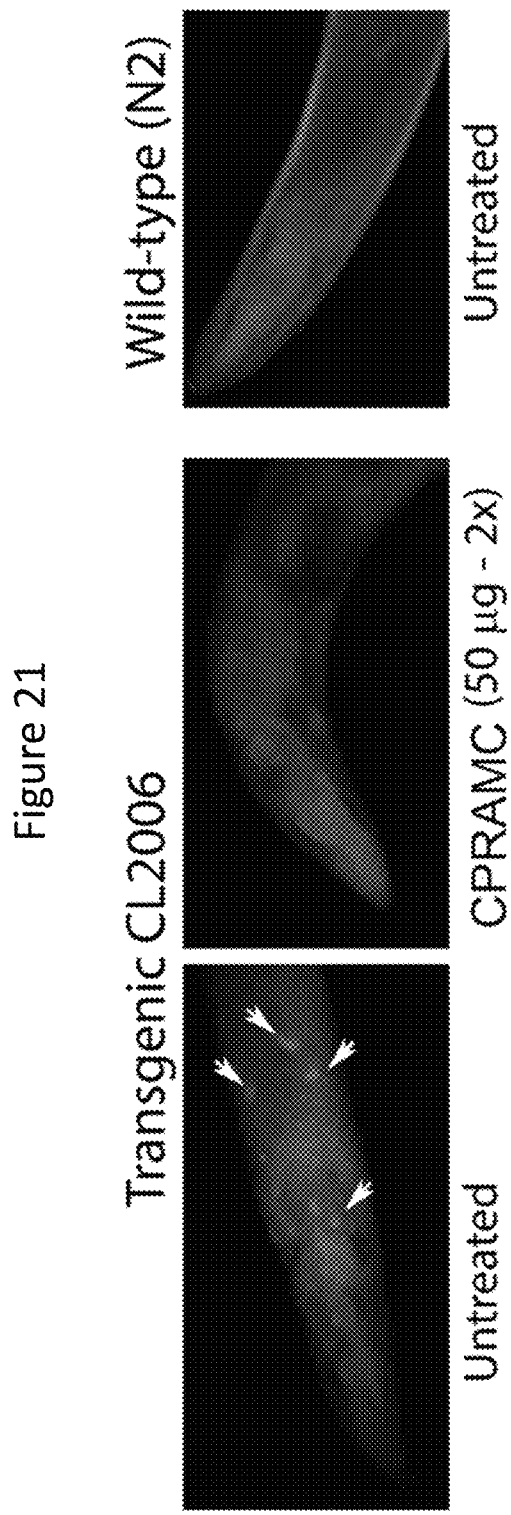
FIG. 21 depicts thioflavin T staining showing Aβ deposits in CPPRAMC treated CL2006 compared to CL2006 and wild type untreated controls.

Thioflavin T staining in CPPRAMC-treated CL2006 and untreated CL2006 and wild type controls shows Aβ deposits (FIG. 21). A reduction of Aβ deposits was seen in CPPRAMC treated CL2006 C. elegans (FIG. 21).

Example 17: Transcriptional Changes in Peptide-treated Worms

Figure 22A:
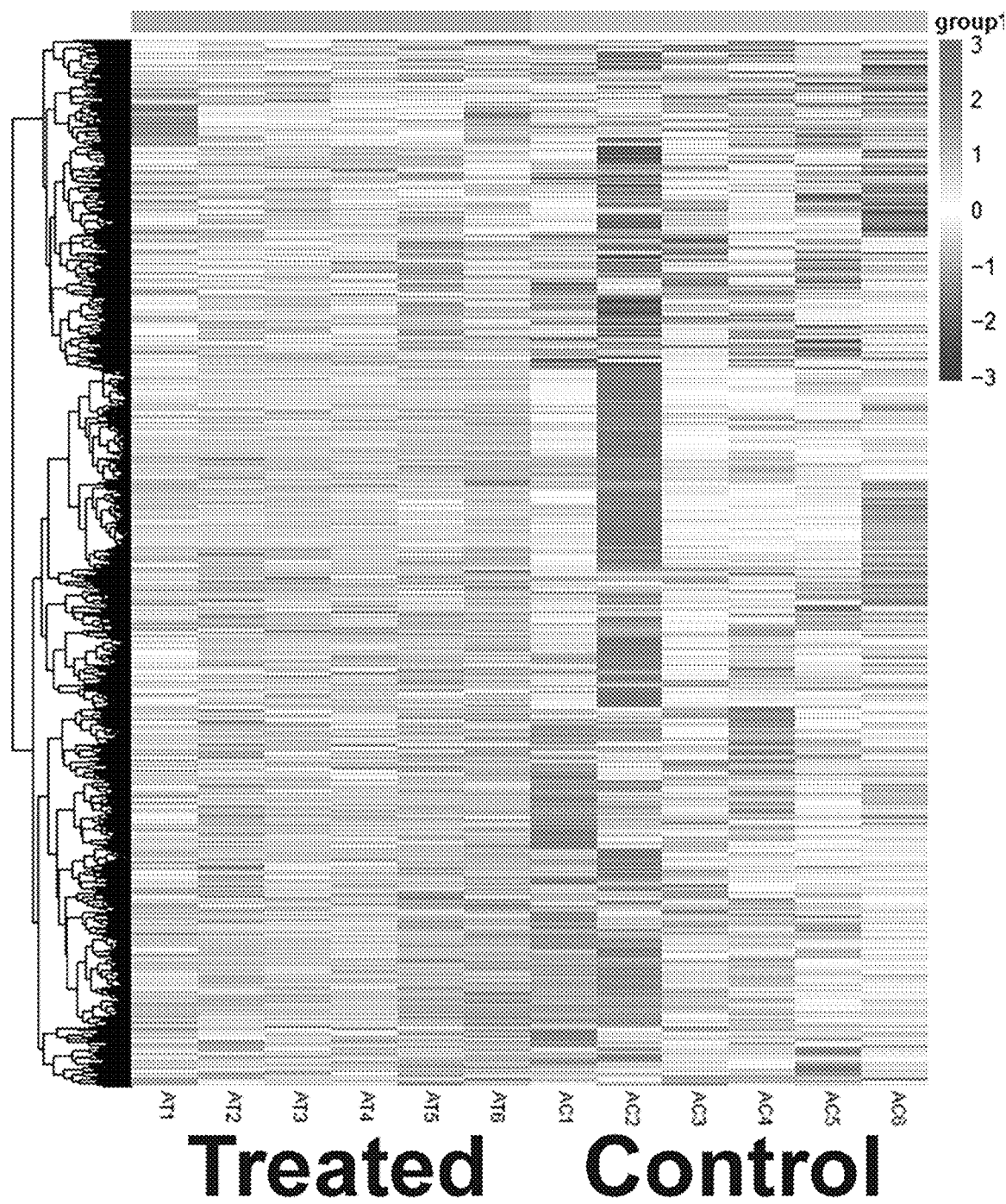
FIG. 22A depicts global transcriptional changes in *C. elegans* in response to CPPRAMC peptide exposure as a hierarchical clustering heatmap. The top of the scale indicates genes with high expression level. The bottom of the scale indicates genes with low expression levels.
Figure 22B:
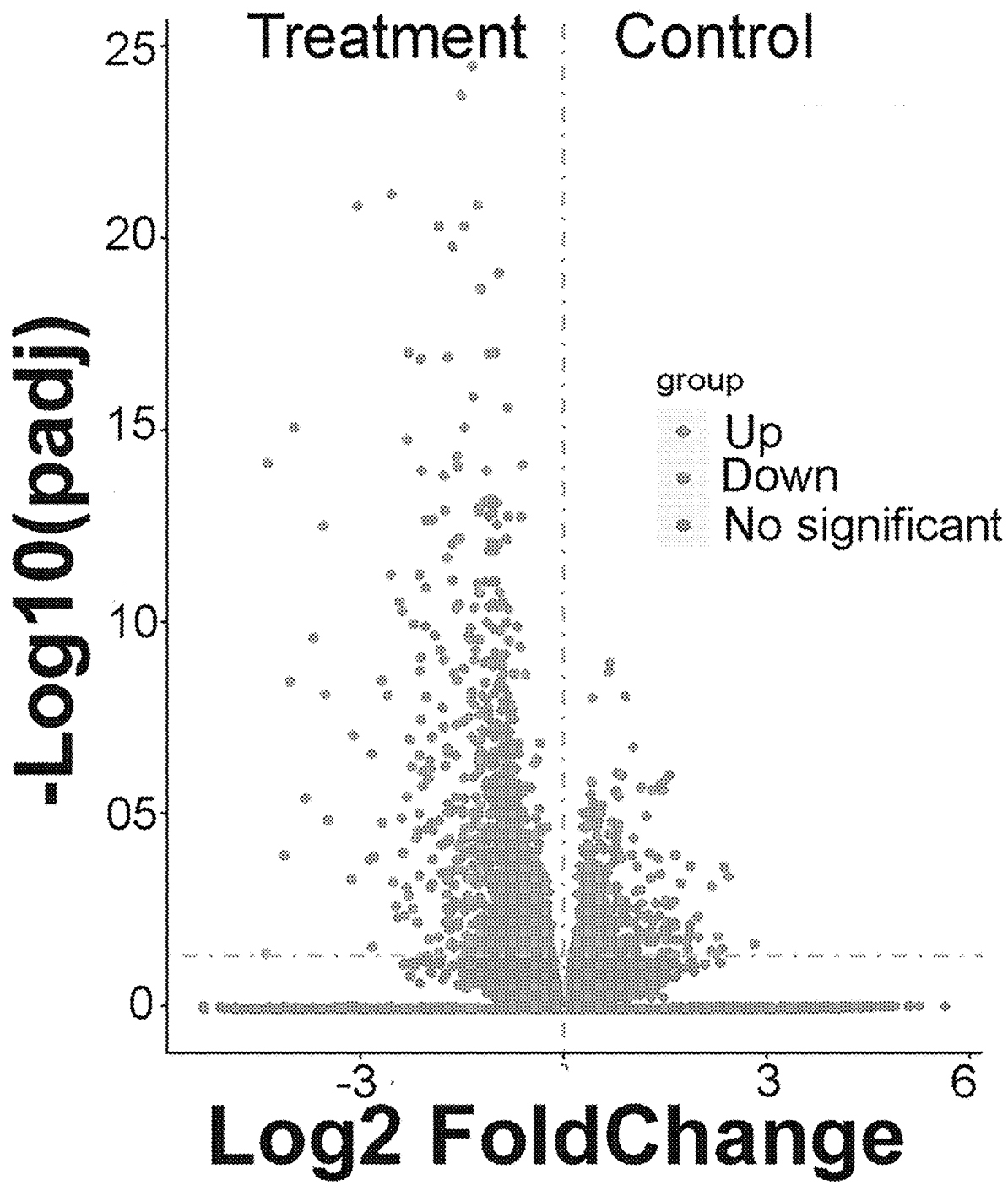
FIG. 22B depicts global transcriptional changes in *C. elegans* in response to CPPRAMC peptide exposure, indicating genes that are significantly up or downregulated with treatment compared to control.

Global transcriptional changes with the application of CPPRAMC peptide were investigated. Global transcriptional changes in C. elegans in response to CPPRAMC peptide exposure were measured and shown as a hierarchical clustering heatmap (FIG. 22A). This data includes genes that are significantly up or downregulated with treatment compared to control (FIG. 22B).

Figure 23:
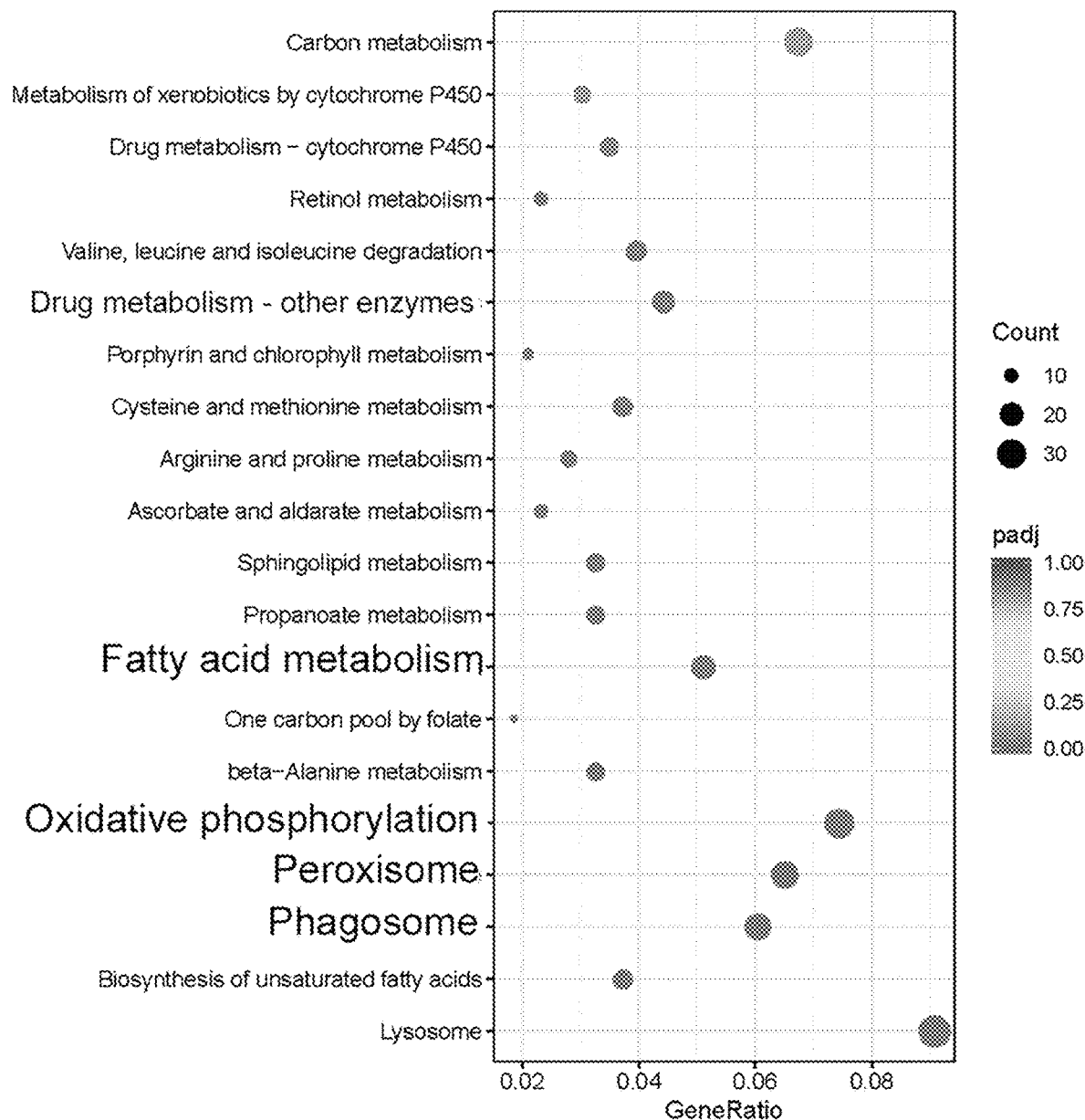
FIG. 23 depicts a KEGG Enrichment Scatter Plot from the global transcriptional changes with pathways associated with differentially expressed genes labeled.

A KEGG Enrichment Scatter Plot of this data shows that the oxidative phosphorylation C. elegans pathway is associated with differentially expressed genes (FIG. 23). Overall, CPPRMC treatment mainly alters the transport and catabolism pathways (cellular processes), energy metabolism pathways, and amino acid metabolism pathways (FIG. 23).

The increased worm lifespan and alleviation of Aβ-induced toxicity up on CPPRAMC treatment are likely mediated by the activation of molecules involved in stress response pathways. These findings signify the therapeutic prospective of CPPRAMC against oxidative stress, aging, and age-concerned Alzheimer's disease.

Example 18: Summary and Assays

Figure 24:
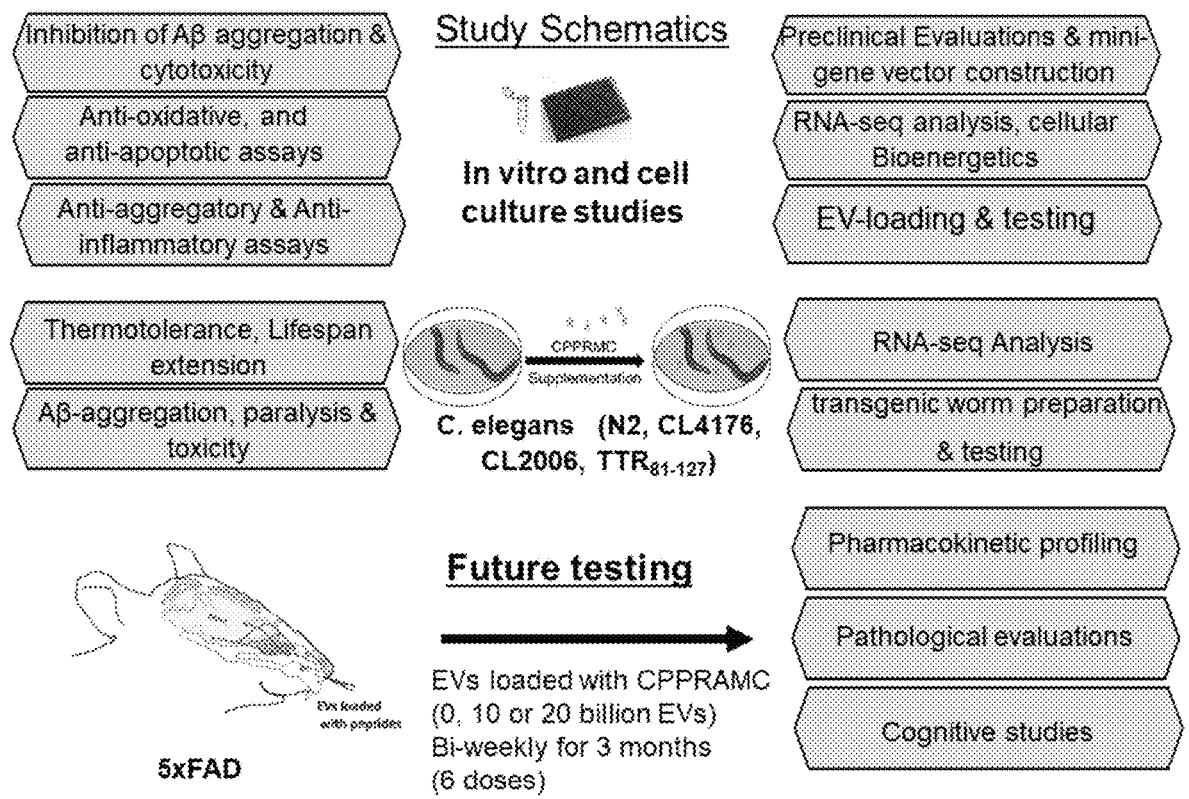
FIG. 24 depicts a summary of study schematics and proposed future testing.

A summary of study schematics and proposed future testing is shown (FIG. 24).

This study evaluated the therapeutic efficacy of CPPRAMCs in treating Alzheimer's disease using cell culture and C. elegans model systems. CPPRAMC affects aged and diseased cells like those found in patients with Alzheimer's disease. In normal cells, CPPRAMC provides a steady pool of ATP-independent chaperones that serve as the first line of passive defense during protein unfolding stresses. It also helps maintain proteostasis and cellular homeostasis and modulates cellular bioenergetics leading to decreased cellular senescence and increased longevity. In aged and diseased cells, CPPRAMC prevents Aβ oligomerization and senile plaque formation. It suppresses ROS buildup and exhibits anti-oxidative properties. It shows anti-apoptotic activity by blocking caspase activation. It suppresses inflammatory processes. It helps to maintain cellular homeostasis and bioenergetics and improves cellular function and survival. Extracellularly, CPPRAMC binds directly to Aβ monomers and oligomers and prevents senile plaque formation. It interacts with toxic misfolded proteins and neutralized them. It also binds to proinflammatory cytokines and exhibits an anti-inflammatory effect.

The peptide also protects ARPE-19 cells from sodium iodate-induced oxidative stress and apoptosis. The CPAMC's block mellitin-induced hemolytic and cytotoxic activities could serve as a therapeutic against bee venom toxin. The test compounds were not toxic to cells but protected ARPE-19 cells from $A\beta_{1-42}$-induced cytotoxicity. C. elegans fed with CPAMC's have higher thermotolerance and live longer. CPAMC's mitigate beta-amyloid oligomerization and deposition in the transgenic C. elegans models of Alzheimer's disease and alleviates Aβ-induced paralysis. Worms maintained with high glucose concentrations, mimicking the hyperglycemic conditions, survived longer when fed with CPAMCs. C. elegans exposed to reactive oxygen species generating compounds like paraquat and juglone survive longer when treated with the amphiphilic peptide. This study shows that CPAMCs can be used to treat protein aggregation diseases and associated pathology.

In conclusion, amphiphilic peptides can suppress the aggregation and accumulation of misfolded proteins and help maintain cellular homeostasis. The amphiphilic peptide protects cells from oxidative stress and prevents apoptosis. CPAMCs prevent Aβ-induced toxicity on cells, and blocks melittin-induced red blood cell hemolysis. The peptide also alleviates Aβ-induced paralysis in a C. elegans model for Alzheimer's disease and increases the worm's lifespan. The amphiphilic peptide improves the life-span of C. elegans maintained with high glucose concentrations to mimic hyperglycemic conditions. These properties display a broad therapeutic potential for amphiphilic peptide chaperones, particularly for paralysis and Alzheimer's disease.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

When introducing elements of the present invention or the embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

The invention claimed is:

1. An amphiphilic peptide chaperone comprising an amino acid sequence having the sequence of LFVIFLVHFSPGRDEDKDEK (SEQ ID NO: 1) or lfviflvhfspgrdedkdek.

2. The amphiphilic peptide chaperone of claim 1, wherein the chaperone further comprises at least one chemical modification selected from the group consisting of myristoylation, phosphorylation, acetylation, methylation, glycosylation, ADP-ribosylation, amidation, lipid addition, oxidation, palmitoylation, FLAG tagging, and tetramethylrhodamine labeling.

3. The amphiphilic peptide chaperone of claim 1, wherein the N-terminus of the amino acid sequence has a $CH_3$ modification and/or the C-terminus of the amino acid sequence has an $NH_2$ modification.

4. A pharmaceutical composition, comprising the amphiphilic peptide chaperone of claim 1.

5. The pharmaceutical composition of claim 4, wherein the amphiphilic peptide chaperone comprises from about 0.001 to about 99.9% of the total weight of the composition.

6. The pharmaceutical composition of claim 4, wherein the chaperone is self-assembled with other like chaperones as spherical nanoparticles.

* * * * *